(12) United States Patent
Suzuki

(10) Patent No.: US 6,665,551 B1
(45) Date of Patent: Dec. 16, 2003

(54) CURRENT DRIVING SYSTEM OF LIGHT EMITTING DIODE

(75) Inventor: Tetsuo Suzuki, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 191 days.

(21) Appl. No.: 09/715,010

(22) Filed: Nov. 20, 2000

(30) Foreign Application Priority Data

Nov. 19, 1999 (JP) .......................................... P. 11-329539

(51) Int. Cl.[7] ................................................ A61B 5/00
(52) U.S. Cl. ...................................... 600/322; 600/310
(58) Field of Search ........................ 600/310, 322–323, 600/309; 356/41; 439/909

(56) References Cited

U.S. PATENT DOCUMENTS 5,818,985 A    10/1998   Merchant et al. .............. 385/20
5,995,855 A  * 11/1999   Kiani et al. .................. 600/310
6,023,541 A  *  2/2000   Merchant et al. .............. 385/20

* cited by examiner

Primary Examiner—Eric F. Winakur
Assistant Examiner—Matthew Kremer
(74) Attorney, Agent, or Firm—Sughrue Mion, PLLC

(57) ABSTRACT

Three current supply lines 44, 45, 41 and connection terminals 32, 34, 30 thereof for respectively driving the light emitting diodes on the probe side are arranged in a light emitting diode driving circuit on the measurement apparatus body side, a pair of driving switches Sw1A, Sw1B and Sw2A, Sw2B for constant current having contact points to be switched to the electric power source side or the ground side are respectively connected with the two current supply lines 44, 45 among the three current supply lines, and switching operation signal supply lines 41A, 42A and 41B, 42B are arranged for successively and continuously driving the light emitting diodes by supplying a switching operation signal for switching the contact points on the electric power source side or on the ground side to the pair of driving switches for constant current.

24 Claims, 17 Drawing Sheets

CURRENT DRIVING SYSTEM OF LIGHT EMITTING DIODE

BACKGROUND OF INVENTION

1. Field of Invention

The present invention relates to a current driving system of a light emitting diode (LED) applied to a measurement apparatus for measuring the concentration of light absorbing material in a living tissue, the measurement apparatus having a main body for calculating the concentration of light absorbing material in a living tissue.

2. Related art

As a common example of the measurement apparatus for measuring the concentration of light absorbing material in a living tissue, there is conventionally provided a pulse oximeter by which the oxygen saturation in arterial blood is measured. This pulse oximeter is known as a measurement apparatus by which the oxygen saturation in arterial blood ($SpO_2$) can be continuously measured non-invasively into an artery by utilizing a variation of blood volume in the artery caused by pulsation.

In this case, the oxygen saturation ($SpO_2$) represents a ratio (%) of hemoglobin contained in blood which is combined with oxygen. Hemoglobin combined with oxygen is referred to as oxyhemoglobin ($HbO_2$), and hemoglobin not combined with oxygen is referred to as deoxyhemoglobin (Hb).

However, red of blood is the color of hemoglobin. Therefore, oxyhemoglobin absorbs less red light, and deoxyhemoglobin absorbs much red light. Accordingly, arterial blood containing much oxygen absorbs less red light because a ratio of oxyhemoglobin is high. Therefore, arterial blood containing much oxygen appears brightly red. On the other hand, venous blood in which oxygen has already been consumed appears dark because it contains much deoxyhemoglobin. As described above, the color of blood reflects the degree of combination of hemoglobin with oxygen, that is, the color of blood reflects the oxygen saturation.

When the pulse oximeter is used, it is possible to obtain only information of arterial blood by using light electric pulses. According to the pulse oximeter, measurement is made in such a manner that a relatively thin portion of a human body such as a finger is irradiated with light and an intensity of transmitted light is measured, that is, light electric pulses are recorded. In this case, the light absorbing characteristic of blood is changed by the oxygen saturation. Even in the case of the pulsation of the same variation of blood volume, the obtained pulse wave amplitude is different according to the oxygen saturation of the blood.

As shown in FIG. 16, in general, the pulse oximeter includes: a probe 10 attached to a patient; and a measurement apparatus body 20. The probe 10 is composed of a light emitting section 12 and a light receiving section 14. A portion of a human body to be measured such as a finger, that is, a living tissue is interposed between the light emitting section 12 and the light receiving section 14. In the light emitting section 12, there are provided two light emitting diodes (LED 1 and LED 2). One is a light emitting diode LED 1, the wave length of the emitted light of which is 660 nm (red light), and the other is a light emitting diode LED 2, the wave length of the emitted light of which is 940 nm (infrared light). On the other hand, a photo-diode is used for the light receiving section 14.

The above two light emitting diodes LED 1 and LED 2 alternately emit light when they are alternately energized by the timing generation circuit 22, which is provided in the measurement apparatus body 20 via the light emitting diode driving circuit 23 at a predetermined timed relation.

As described above, rays of light are outputted from the respective light emitting diodes LED 1 and LED 2 in the light emitting section 12 and transmitted through a living tissue such as a finger 16. Then the rays of light arrive at the light receiving section 14. Intensities of these rays of light, the wave lengths of which are 660 nm and 940 nm, are converted into currents by the photo-diodes. The thus obtained currents are converted into voltages by the current/voltage converter 24 arranged in the measurement apparatus body 20. At the same time, these signals are separated into transmitted light signals of the respective wave lengths by the demodulator 25.

Then, the pulse wave components ($\Delta A660$, $\Delta A940$) of each absorbance are taken out from the two transmitted light signals, which have been obtained by the demodulator 25, by the pulse wave component detectors 26a, 26b of each wave length. Ratio $\Phi$ of absorbance ($=\Delta A660/\Delta A940$) is calculated by the absorbance ratio calculator 27. Further, the oxygen saturation S [$=f(\Phi)$] is converted by the oxygen saturation converter 28.

However, the pulse oximeter has come into wide use as a vital sign signal monitor, because it is possible for the pulse oximeter to make a continuous non-invasive measurement and further it is unnecessary to make a calibration by principle when the pulse oximeter is used, that is, the pulse oximeter meets the essential requirements necessary for the monitor to be used for monitoring a condition of a patient. Accordingly, various pulse oximeters, in which the apparatus arrangement shown in FIG. 14 is used, are manufactured and sold by a large number of manufacturers nowadays.

For example, as a lead connection system for connecting the probe 10 with the measurement apparatus body 20 in the conventional pulse oximeter in which two light emitting diodes are used, there are provided two lead connection systems. One is a three line system shown in FIG. 17, and the other is a two line system shown in FIG. 18.

As shown in FIG. 17, in the three line connection system, two light emitting diodes LED 1 and LED 2 are connected in parallel to each other by the common line LED-COMMON and two driving lines LED-DRV1, LED-DRV2. As shown in FIG. 18, in the two line connection system, two light emitting diodes LED 1 and LED 2 are connected in reverse-parallel to each other by two driving lines LED-DRV1, LED-DRV2.

As a variation of the lead connection system, there is provided a lead connection system in which four light emitting diodes LED 1 to LED 4 are connected by the three line system as shown in FIG. 19. Also, there is provided a lead connection system in which three light emitting diodes LED 1 to LED 3 are connected by the three line system as shown in FIG. 20. In the lead connection system shown in FIG. 20, one of the light emitting diodes incorporated into the lead connection system shown in FIG. 19 is omitted.

In this case, for example, in the pulse oximeter in which the three line type lead connection system is used, it is preferable that the three line type probe and the two line type probe can be connected with one measurement apparatus body being compatible with each other and the light emitting diode of each probe can be appropriately driven. However, although the light emitting diode in the three line type probe and the light emitting diode in the two line type probe respectively have two driving lines LED-DRV1 and LED-DRV2, their electrical connection system are different from each other. Therefore, the three line type probe and the two line type probe are not compatible with each other, that is, it is impossible to appropriately drive the light emitting diode of each lead connection system with compatibility.

SUMMARY OF INVENTION

It is an object of the present invention to provide a current driving system of a light emitting diode provided in that: only when a simple additional circuit is arranged in a light emitting diode driving circuit, various probes can be used being made compatible with each other when they are connected with the measurement apparatus body without changing the basic structure of the circuit of the measurement apparatus body and without providing a redundant connection means and without being restricted by the lead connection system of the light emitting diode on the probe side.

In order to accomplish the above objects, the present invention provides a current driving system of a light emitting diode including an apparatus for measuring the concentration of light absorbing material in a living tissue, the apparatus for measuring the concentration of light absorbing material having a probe attached to the living tissue and also having a measurement apparatus body combined with the probe for calculating the concentration of light absorbing material in the living tissue, the probe having a light emitting section composed of at least two light emitting diodes of different wave lengths of emitted light and also having a light receiving section composed of a photo-diode for receiving light emitted from the light emitting section and transmitted through the living tissue, the light emitting diodes being successively and continuously driven by a light emitting diode driving circuit arranged in the measurement apparatus body, the current driving system of a light emitting diode provided in that:

three current supply lines and connection terminals thereof for respectively driving the light emitting diodes on the probe side are arranged in a light emitting diode driving circuit on the measurement apparatus body side;

a pair of driving switches having contact points to be switched to the electric power source side or the ground side are respectively connected with the two current supply lines among the three current supply lines; and switching operation signal supply lines are arranged for successively and continuously driving the light emitting diodes by supplying a switching operation signal for switching the contact points on the electric power source side or on the ground side to the pair of driving switches.

In this case, the three current supply lines for respectively driving the light emitting diodes are respectively connected with the first driving line and the second driving line of the probe and also connected with the common line so that at least two light emitting diodes can be successively and continuously driven on the probe side.

The switching operation signal supply line is connected and arranged so that the light emitting diodes can be successively and continuously driven when a contact point switching operation is simultaneously conducted on the contact point of one pair of driving switches by which switching is made onto the electric power source side and also conducted on the contact point of the other pair of driving switches by which switching is made onto the ground side with respect to each pair of driving switches and also when a contact point switching operation is simultaneously conducted on the contact point of one pair of driving switches by which switching is made onto the ground side and also conducted on the contact point of the other pair of driving switches by which switching is made onto the electric power source side with respect to each pair of driving switches.

The three current supply lines for respectively driving the light emitting diodes are respectively connected with the first driving line and the second driving line of the probe and the other current supply line is in an unconnected state with the probe. In this case, the terminal of the unconnected current supply line is arranged as a dummy terminal, which is not used.

The switching operation signal supply line is connected and arranged so that the contact points switched and connected with the electric power side and the ground side of the respective driving switches can be independently switched by the pair of driving switches respectively connected with the two current supply lines, the third driving switch having a contact point for switching between the electric power source side and the ground side is arranged in the other current supply line, and a switching operation signal supply line is connected and arranged which is used for switching the contact point of the third driving switch corresponding to the switching signal supplied to the switching signal supply line of the pair of driving switch.

The three current supply lines for respectively driving the light emitting diodes are composed in such a manner that three or four light emitting diodes, in which on the probe side two light emitting diodes are connected in reverse-parallel to each other and one or two light emitting diodes are connected with each other in parallel to them in reverse-parallel to each other, are respectively connected with the first driving line and the second driving line, which are successively and continuously driven, and also connected with the common line.

The probe is composed in such a manner that reverse-parallel diodes are connected between the common line and one driving line, and the reverse-parallel diodes are connected with the common line and the other driving line, so that the four light emitting diodes are respectively, successively and continuously driven.

The probe is composed in such a manner that reverse-parallel diodes are connected between the common line and one driving line, and the diodes are connected with the common line and the other driving line, so that the three light emitting diodes are respectively, successively and continuously driven.

The switching operation signal supply line is connected and arranged so that the contact points switched and connected with the electric power side and the ground side of the respective driving switches can be independently switched by the pair of driving switches respectively connected with the two current supply lines, the third driving switch having a contact point for switching between the electric power source side and the ground side is arranged in the other current supply line, and a switching operation signal supply line is connected and arranged which is used for switching the contact point of the third driving switch corresponding to the switching signal supplied to the switching signal supply line of the pair of driving switch.

Four switching operation signal supply lines are respectively connected and arranged as a switching operation signal supply line for switching the contact points of the pair of driving switches respectively connected with the two current supply lines and also as a switching operation signal supply line for switching the contact points of the third driving switch.

The present invention provides a current driving system of a light emitting diode including an apparatus for measuring the concentration of light absorbing material in a living tissue, the apparatus for measuring the concentration of light absorbing material having a probe attached to the living tissue and also having a measurement apparatus body combined with the probe for calculating the concentration of light absorbing material in the living tissue, the probe having a light emitting section composed of at least two light emitting diodes of different wave lengths of emitted light and also having a light receiving section composed of a photo-diode for receiving light emitted from the light emitting section and transmitted through the living tissue, the light emitting diodes being successively and continuously driven by a light emitting diode driving circuit arranged in the measurement apparatus body, the current driving system of a light emitting diode provided in that:

- a predetermined number of current supply lines and connection terminals thereof for respectively driving the light emitting diodes on the probe side are arranged in a light emitting diode driving circuit on the measurement apparatus body side;
- driving switches having contact points to be switched onto the electric power source side or the ground side are connected with the predetermined number of current supply lines in the current supply lines;
- the probe is compatible with a probe, the number of light emitting diodes of which is different, and also compatible with a probe, the connection system of which is different; and
- a switching operation signal supply line for switching the driving switch so as to successively and continuously drive the light emitting diodes is arranged.

The driving switch may be composed of an ON-OFF switch and a switch for constant current.

DETAILED DESCRIPTION OF PREFERRED EMBODIMENTS

Principal of Invention

The present inventors found the following knowledge. When a predetermined additional circuit is arranged in a connecting section of the light emitting diode driving circuit with which the probe of the measurement apparatus body is connected, the two line type probe and the three line type probe can be made compatible with each other when they are connected with the measurement apparatus body without changing the basic structure of the circuit of the measurement apparatus body and without providing a redundant connection means.

That is, the above problems can be solved by providing a current driving system of a light emitting diode provided in that: three current supply lines and connection terminals thereof for respectively driving the light emitting diodes on the probe side are arranged in a light emitting diode driving circuit on the measurement apparatus body side; a pair of driving switches having contact points to be switched to the electric power source side or the ground side are respectively connected with the two current supply lines among the three current supply lines; and a switching operation signal supply line for successively and continuously driving the light emitting diodes alternately by supplying a switching operation signal for switching the contact points on the electric power source side or on the ground side to the pair of driving switches is arranged.

Next, referring to the appended drawings, embodiments of a current driving system of a light emitting diode of the present invention will be explained in detail as follows. In this connection, the current drive system of a light emitting diode of the present invention is generally applied to an apparatus for measuring the concentration of light absorbing material. However, in the following embodiments, explanations will be made into a current driving system of a light emitting diode applied to a pulse oximeter.

First Embodiment

Figure 1:
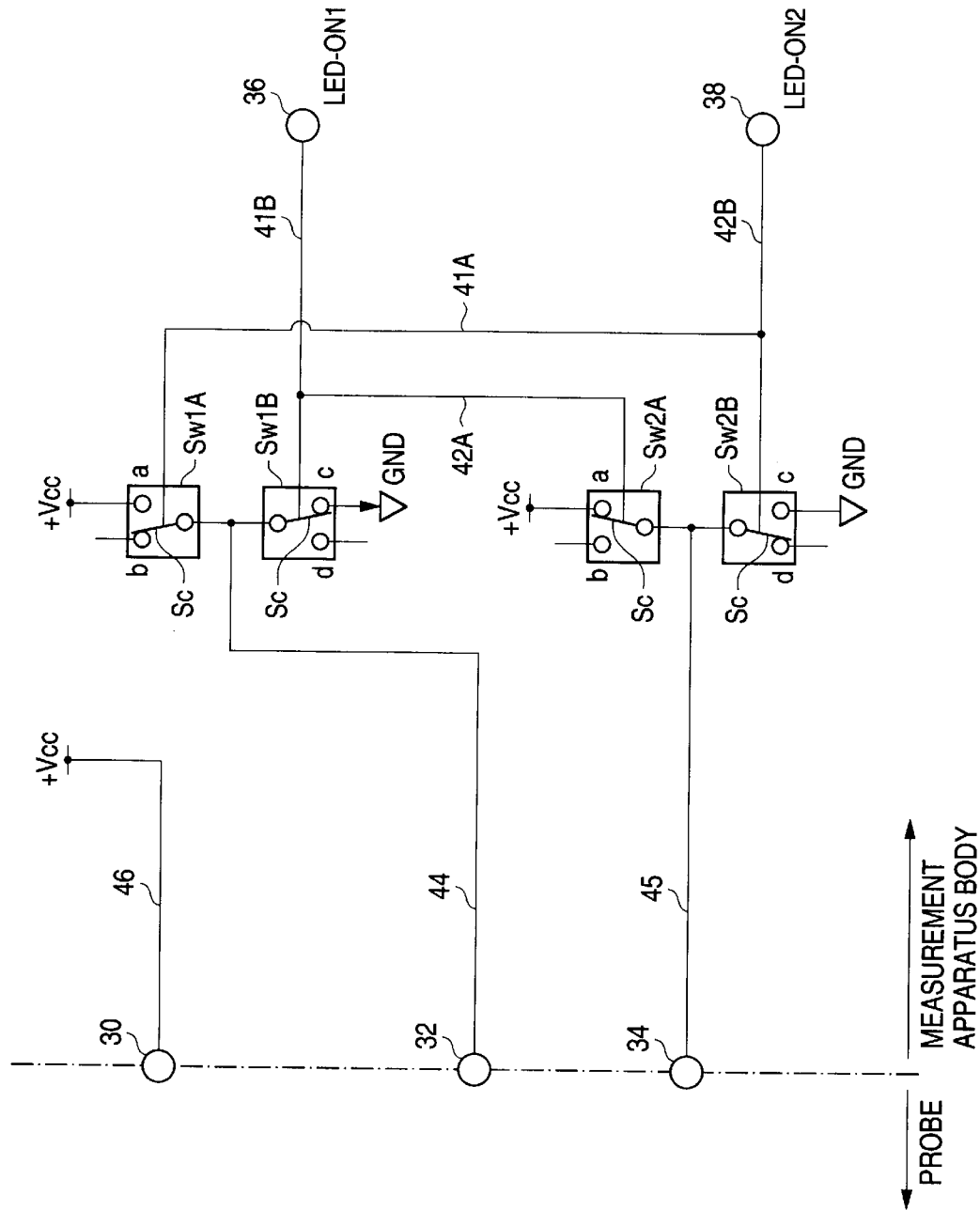
FIG. 1 is a schematic illustration showing an outline of a current driving system of a light emitting diode, which is an embodiment of a current driving system of a light emitting diode of the present invention, in which two light emitting diodes connected by the three line type or the two line type connection is connected with the common measurement apparatus body so that the respective light emitting diodes can be alternately driven.

FIG. 1 is a connection diagram showing an embodiment of a current driving system of a light emitting diode of the present invention. That is, FIG. 1 shows an outline of a current driving system of a light emitting diode applied to a pulse oximeter in which the probe side composed of two light emitting diodes connected by the three line type or the two line type connection is connected with the common measurement apparatus body side so that the respective light emitting diodes can be alternately driven.

In FIG. 1, reference numeral 30 is a connection terminal of common line LED-COMMON provided on the measurement apparatus body side. Reference numeral 32 is a connection terminal of the first drive line LED-DRV1 for the first light emitting diode provided on the measurement apparatus body side. Reference numeral 34 is a connection terminal of the second drive line LED-DRV2 for the second light emitting diode.

There are provided a pair of driving switches Sw1A, Sw2A for constant current on the electric power side and a pair of driving switches Sw1B, Sw2B for constant current on the electric ground side. These driving switches for constant current are connected with the connection terminal 32 of the first drive line LED-DRV1 and the connection terminal 34 of the second drive line LED-DRV2 respectively connected with +Vcc on the electric power source side and GND on the ground side via the electric current supply lines 44, 45. In this connection, the connection terminal 30 of the common line LED-COMMON is directly connected with +Vcc on the electric power source side via the electric current supply line 46. Contact points "a" of switching contact pieces Sc of the driving switches Sw1A, Sw2A for constant current on the electric power side are connected with +Vcc on the electric power side, and contact points "b" are open. Contact points "c" of switching contact pieces Sc of the driving switches Sw1B, Sw2B for constant current on the ground side are connected with GND on the ground side, and contact points "d" are open.

Concerning the switching contact pieces Sc of the driving switches Sw1A, Sw1B for constant current and the driving switches Sw2A, Sw2B for constant current, in order to respectively switch between contact points "a" and "b" and also switch between contact points "c" and "d", there are provided switching operation signal lines 41A, 41B, 42A, 42B which are connected with the first switching operation signal input terminal 36 and the second switching operation signal input terminal 38 arranged on the measurement apparatus body side. The signal line 41A connected with the driving switch Sw1A for constant current on the electric power source side and the signal line 42B connected with the driving switch Sw2B for constant current on the ground side are connected with the second switching operation signal input terminal 38 which is commonly used. The signal line 41B connected with the driving switch Sw1B for constant current on the ground side and the signal line 42A connected with the driving switch Sw2A for constant current on the electric power source side are connected with the first switching operation signal input terminal 36 which is commonly used.

Next, referring to FIGS. 2, 3, 4 and 5, operation of the current driving system of a light emitting diode composed as described above will be explained below.

Figure 2:
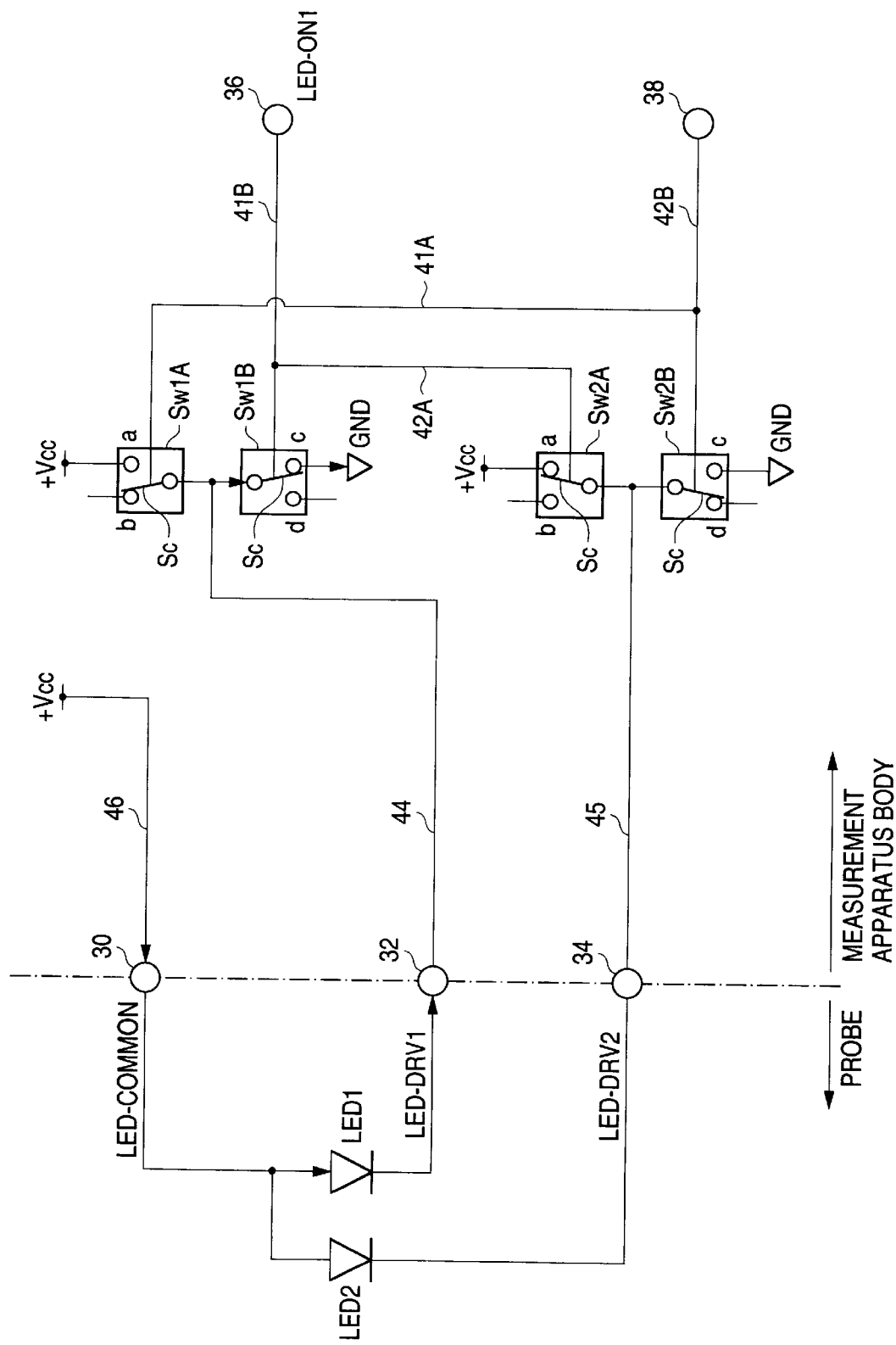
FIG. 2 is a schematic illustration showing a state in which one of the two light emitting diodes connected by the three line type connection system is driven in the current driving system shown in FIG. 1.
Figure 3:
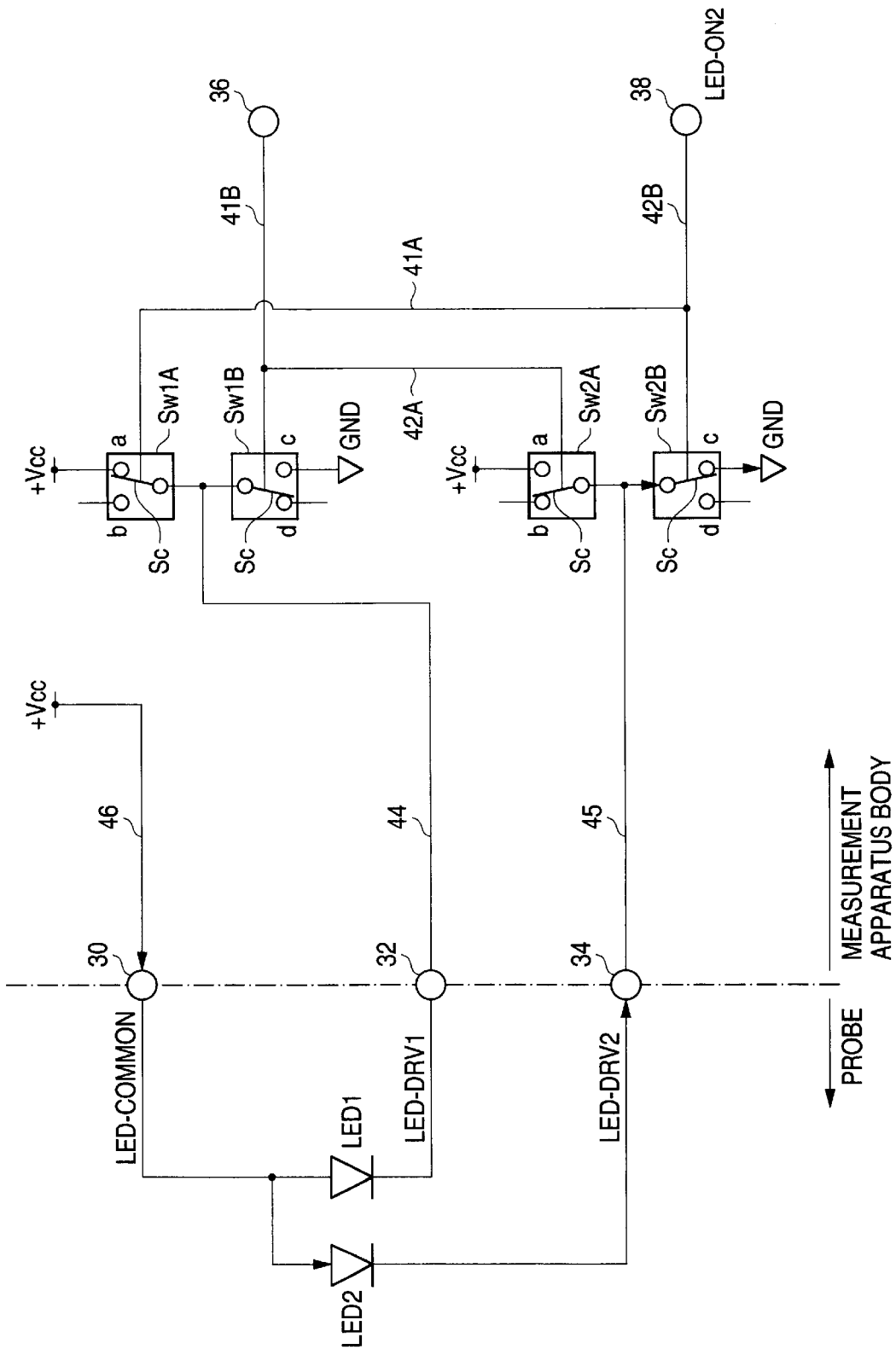
FIG. 3 is a schematic illustration showing a state in which the other of the two light emitting diodes connected by the three line type connection system in FIG. 2 is driven.

Driving System of Two Light Emitting Diodes Connected by Three Line Connection Method FIGS. 2 and 3 are connection diagrams showing a current driving system for driving two light emitting diodes LED 1, LED 2 which are connected by the three line connection method on the probe side. Referring to FIG. 2, first, when the switching operation signal LED-ON1 is supplied to the first switching operation signal input terminal 36, the switching contact piece Sc of the driving switch Sw1A for constant current on the electric power source side is connected with the contact point "b", and the switching contact piece Sc of the driving switch Sw2A for constant current on the electric power source side is connected with the contact point "a". In this case, the switching contact piece Sc of the driving switch Sw1B for constant current on the ground side is connected with the contact point "c", and the switching contact piece Sc of the driving switch Sw2B for constant current on the ground side is connected with the contact point "d". Due to the foregoing, a driving current supplied from the electric power source +Vcc on the measurement apparatus body side to the light emitting diode flows in the current supply line 46 via the first light emitting diode LED 1 and further flows into the driving switch Sw1B for constant current on the ground side via the connection terminal 32 of the first driving line LED-DRV1 and the current supply line 44. Therefore, the first light emitting diode LED 1 can be driven.

Next, in FIG. 3, when the switching operation signal LED-ON2 is supplied to the second switching operation signal input terminal 38, the switching contact piece Sc of the driving switch Sw1A for constant current on the electric power side is connected with the contact point "a", and the switching contact piece Sc of the driving switch Sw2A for constant current on the electric power side is connected with the contact point "b". In this case, the switching contact piece Sc of the driving switch Sw1B for constant current on the ground side is connected with the contact point "d", and the switching contact piece Sc of the driving switch Sw2B for constant current on the ground side is connected with the contact point "c". Due to the foregoing, a driving current supplied from the electric power source +Vcc on the measurement apparatus body side to the light emitting diode flows in the current supply line 46 via the connection terminal 30 of the common line LED-COMMON and the first light emitting diode LED 2 and further flows into the driving switch Sw2B for constant current on the ground side via the connection terminal 34 of the second driving line LED-DRV2 and also via the current supply line 45. In this way, the second light emitting diode LED 2 can be driven.

When the above operation is repeated with a predetermined timed relation, the two light emitting diodes, which are connected by the three line connection method, can be alternately driven.

Figure 4:
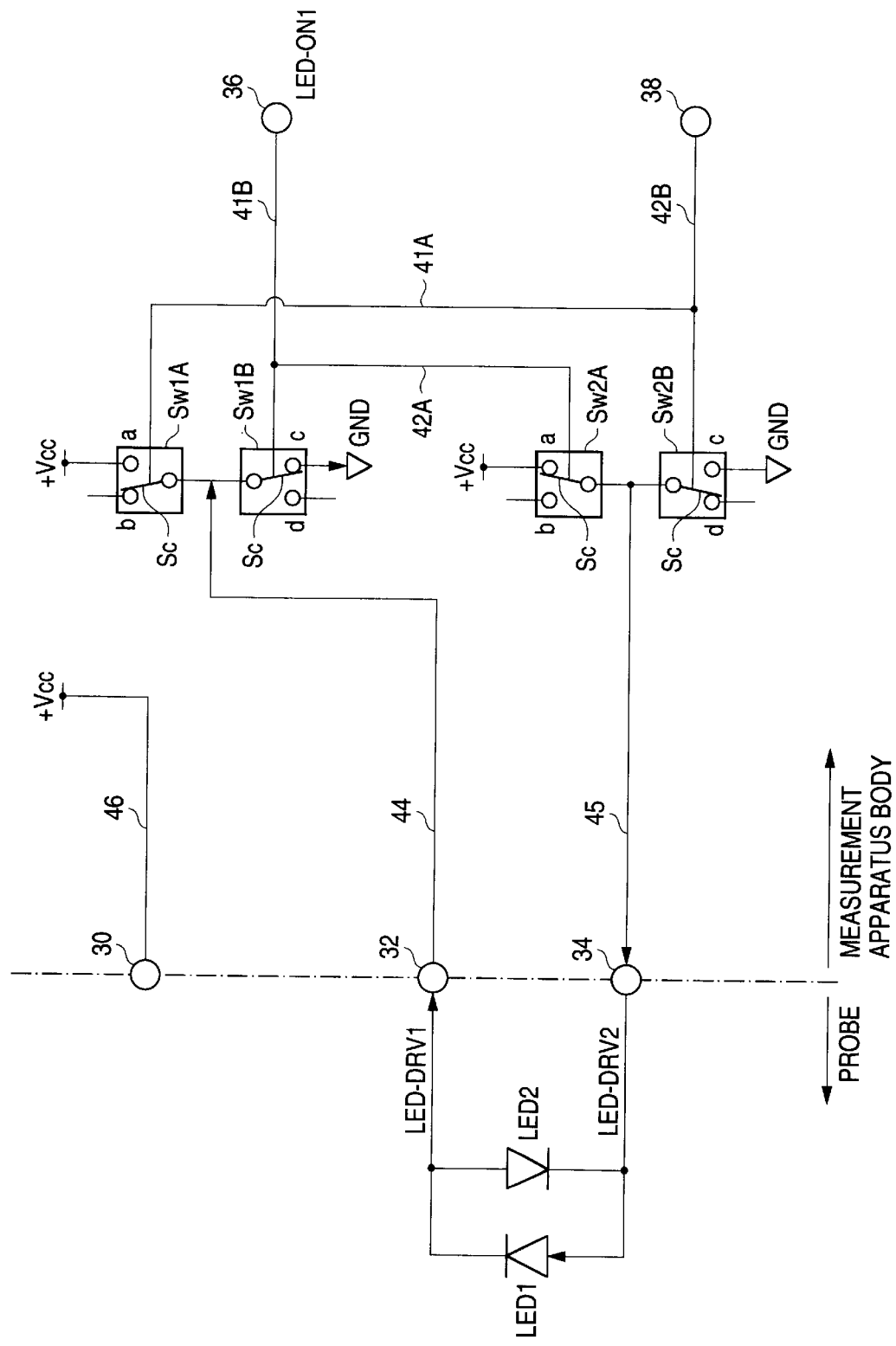
FIG. 4 is a schematic illustration showing a state in which one of the two light emitting diodes connected by the two line type connection system is driven in the current driving system shown in FIG. 1.
Figure 5:
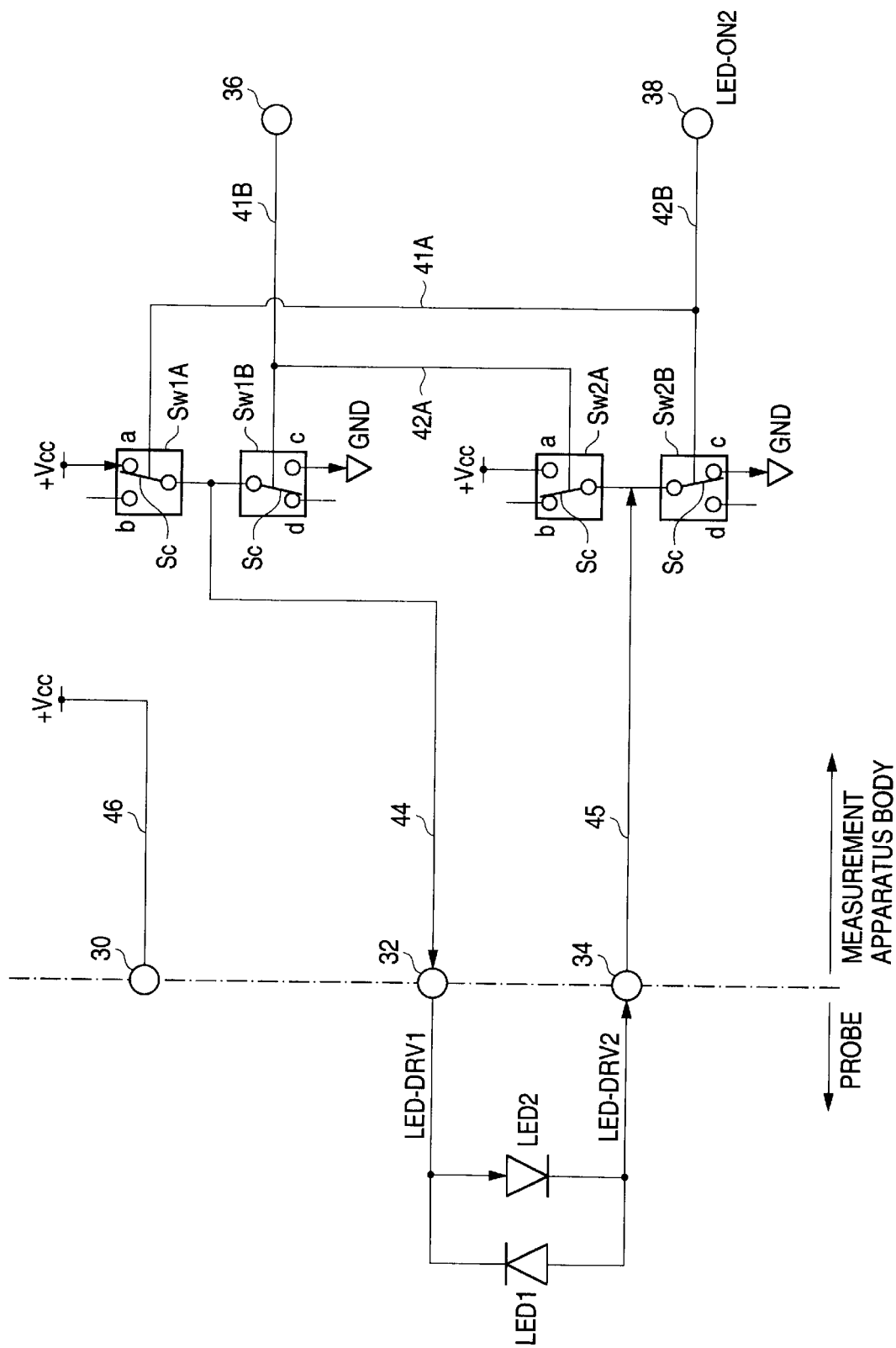
FIG. 5 is a schematic illustration showing a state in which the other of the two light emitting diodes connected by the two line type connection system shown in FIG. 4 is driven.

Driving System of Two Light Emitting Diodes Connected by Two Line Connection Method FIGS. 4 and 5 are connection diagrams showing a current driving system for driving two light emitting diodes LED 1, LED 2 which are connected by the two line connection method on the probe side. In this case, the connection terminal 30 of the common line LED-COMMON provided on the current supply line 46 directly connected with the electric power supply +Vcc on the measurement apparatus body side is a dummy terminal, which is not used. In this case, in FIG. 4, when the switching operation signal LED-ON1 is supplied to the first switching operation signal input terminal 36, the switching contact piece Sc of the driving switch Sw1A for constant current on the electric power source side is connected with the contact point "b", and the switching contact piece Sc of the driving switch Sw2A for constant current on the electric power source side is connected with the contact point "a". In this case, the switching contact piece Sc of the driving switch Sw1B for constant current on the ground side is connected with the contact point "c", and the switching contact piece Sc of the driving switch Sw2B for constant current on the ground side is connected with the contact point "d". Due to the foregoing, a driving current supplied from the electric power source +Vcc on the measurement apparatus body side to the light emitting diode flows from the driving switch Sw2A for constant current on the electric power source side via the current supply line 45 and the connection terminal 34 of the second driving line LED-DRV2 and flows into the driving switch Sw1B for constant current on the ground side via the first light emitting diode LED 1, the connection terminal 32 of the first driving line LED-DRV1 and the current supply line 44. In this way, the first light emitting diode LED 1 can be driven.

Next, in FIG. 5, when the switching operation signal LED-ON2 is supplied to the second switching operation signal input terminal 38, the switching contact piece Sc of the driving switch Sw1A for constant current on the electric power source side is connected with the contact point "a", and at the same time the switching contact piece Sc of the driving switch Sw2A for constant current on the electric power source side is connected with the contact point "b". In this case, the switching contact piece Sc of the driving switch Sw1B for constant current on the ground side is connected with the contact point "d", and at the same time the switching contact piece Sc of the driving switch Sw2B for constant current on the ground side is connected with the contact point "c". Due to the foregoing, a driving current, which is supplied from the electric power source +Vcc on the measurement apparatus body side to the light emitting diode, flows from the driving switch Sw1A for constant current on the electric power source side to the driving switch Sw2B for constant current on the ground side via the current supply line 44, the connection terminal 32 of the first driving line LED-DRV1, the second light emitting diode LED 2, the connection terminal 34 of the second driving line LED-DRV2 and the current supply line 45. In this way, the second light emitting diode LED 2 can be driven.

When the above operation is repeated with a predetermined timed relation, the two light emitting diodes, which are connected by the two line connection method, can be alternately driven.

Second Embodiment

Figure 6:
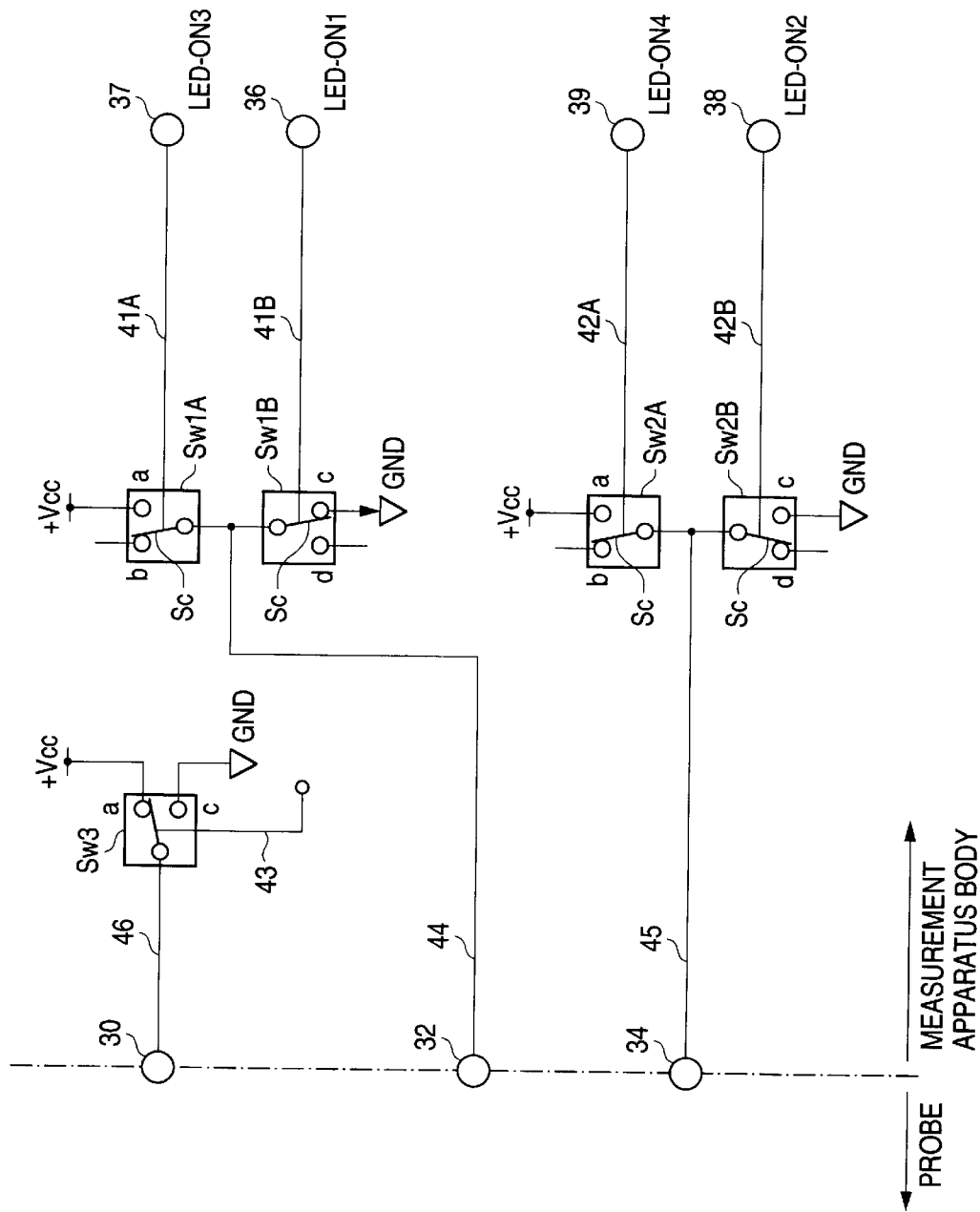
FIG. 6 is a schematic illustration showing another embodiment of a current driving system of the present invention in which four light emitting diodes connected by the three line type connection system are connected with the measurement apparatus body so as to drive the light emitting diodes.

FIG. 6 is a connection diagram showing another embodiment of a current driving system of a light emitting diode of the present invention. FIG. 6 is a schematic illustration for explaining an outline of a driving system to drive each light emitting diode when four light emitting diodes, which are connected by the three line connection method on the probe side, are connected with the common measurement apparatus body. In this case, for the convenience of explanations, like reference characters are used to indicate like parts in FIGS. 1 to 5 showing Embodiment 1 and FIG. 6.

As shown in FIG. 6, in this embodiment, the third driving switch Sw3 for constant current is arranged in the current supply line 46 by which the connection terminal 30 of the common line LED-COMMON is directly connected with +Vcc on the electric power source side. In this case, in the switching contact piece Sc of the third driving switch Sw3 for constant current, the contact point "a" is connected with +Vcc on the electric power source side, and the contact point "c" is connected with GND on the ground side. Concerning the switching contact piece Sc of the third driving switch Sw3 for constant current, the switching operation signal line 43 is connected so that switching can be conducted between the contact points "a" and "c".

Concerning the switching contact pieces Sc of a pair of driving switches Sw1A, Sw2A for constant current on the electric power source side and a pair of driving switches Sw1B, Sw2B for constant current on the ground side, in order to conduct switching between the contact points "a" and "b" and also between the contact points "c" and "d", the switching operation signal lines 41A, 41B, 42A, 42B are respectively connected. These switching operation signal lines 41A, 41B, 42A, 42B are respectively connected with the third switching operation signal input terminal 37, the first switching operation signal input terminal 36, the fourth switching operation signal input terminal 39 and the second switching operation signal input terminal 38.

Next, referring to FIGS. 7 to 10, operation of the current driving system of a light emitting diode composed as described above will be explained below.

Figure 7:
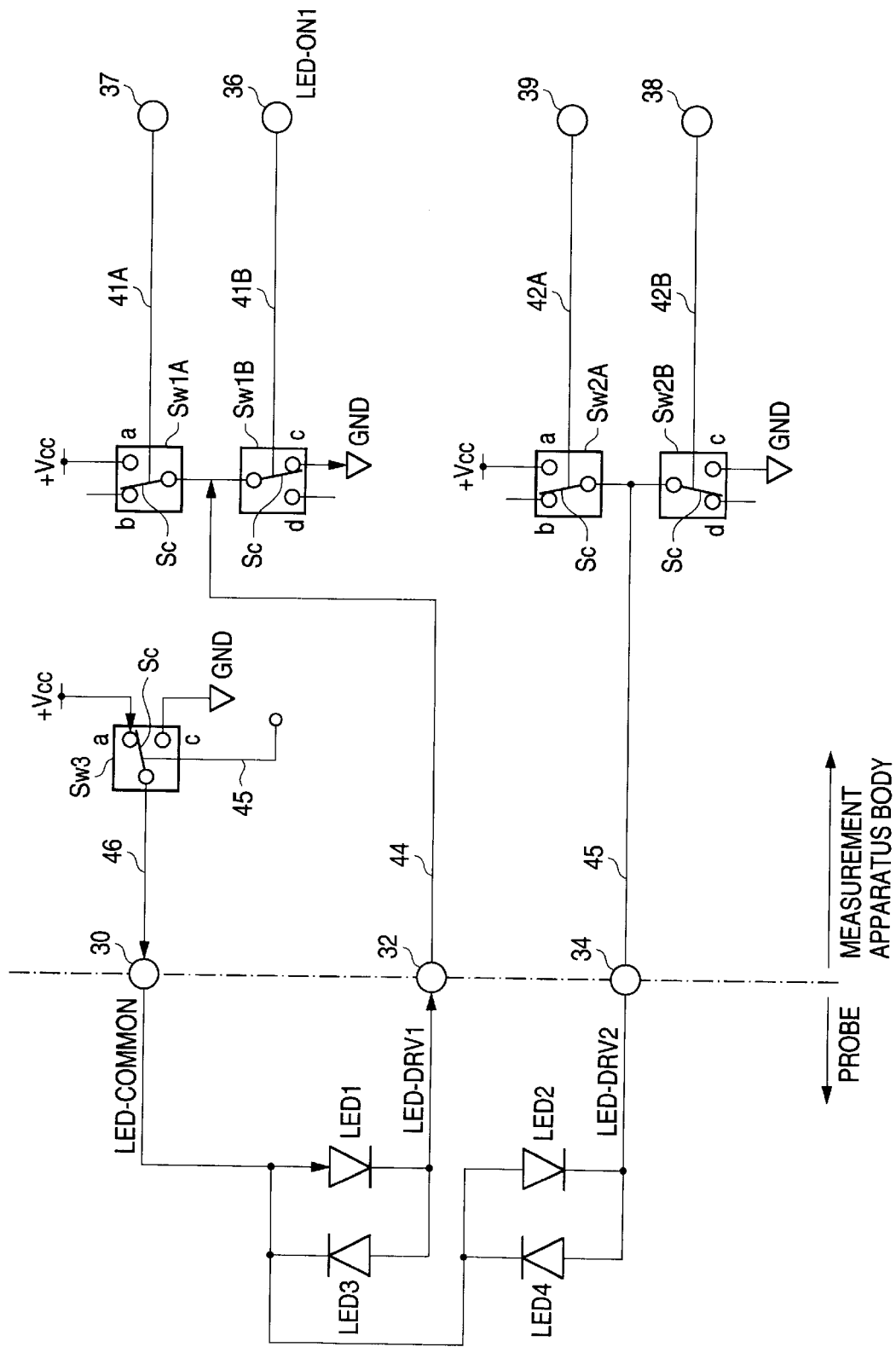
FIG. 7 is a schematic illustration showing a state in which the first light emitting diode out of the four light emitting diodes connected by the three line type connection system in the current driving system shown in FIG. 6 is driven.

Driving System of Four Light Emitting Diodes Connected by Three Line Connection Method FIGS. 7 to 10 are connection diagrams showing a current driving system for driving four light emitting diodes LED 1 to LED 4 which are connected by the three line connection method on the probe side. Referring to FIG. 7, when the switching operation signal LED-ON1 is supplied to the first switching operation signal input terminal 36, the switching contact piece Sc of the driving switch Sw1B for constant current on the ground side is connected with the contact point "c", and the switching contact piece Sc of the third driving switch Sw3 for constant current is connected with the contact point "a" by the switching operation signal LED-ON1 supplied via the switching operation signal line 43. In this case, the switching contact pieces Sc of the driving switches Sw1A, Sw2A and Sw2B for constant current are respectively connected with the open contact points "b", "b" and "d". Due to the foregoing, a driving current supplied from the electric power source +Vcc on the measurement apparatus body side to the light emitting diode flows in the current supply line 46 via the connection terminal 30 of the common line LED-COMMON and the first light emitting diode LED 1 and further flows into the driving switch Sw1B for constant current on the ground side via the connection terminal 32 of the first driving line LED-DRV1 and the current supply line 44. Therefore, the first light emitting diode LED 1 can be driven.

Figure 8:
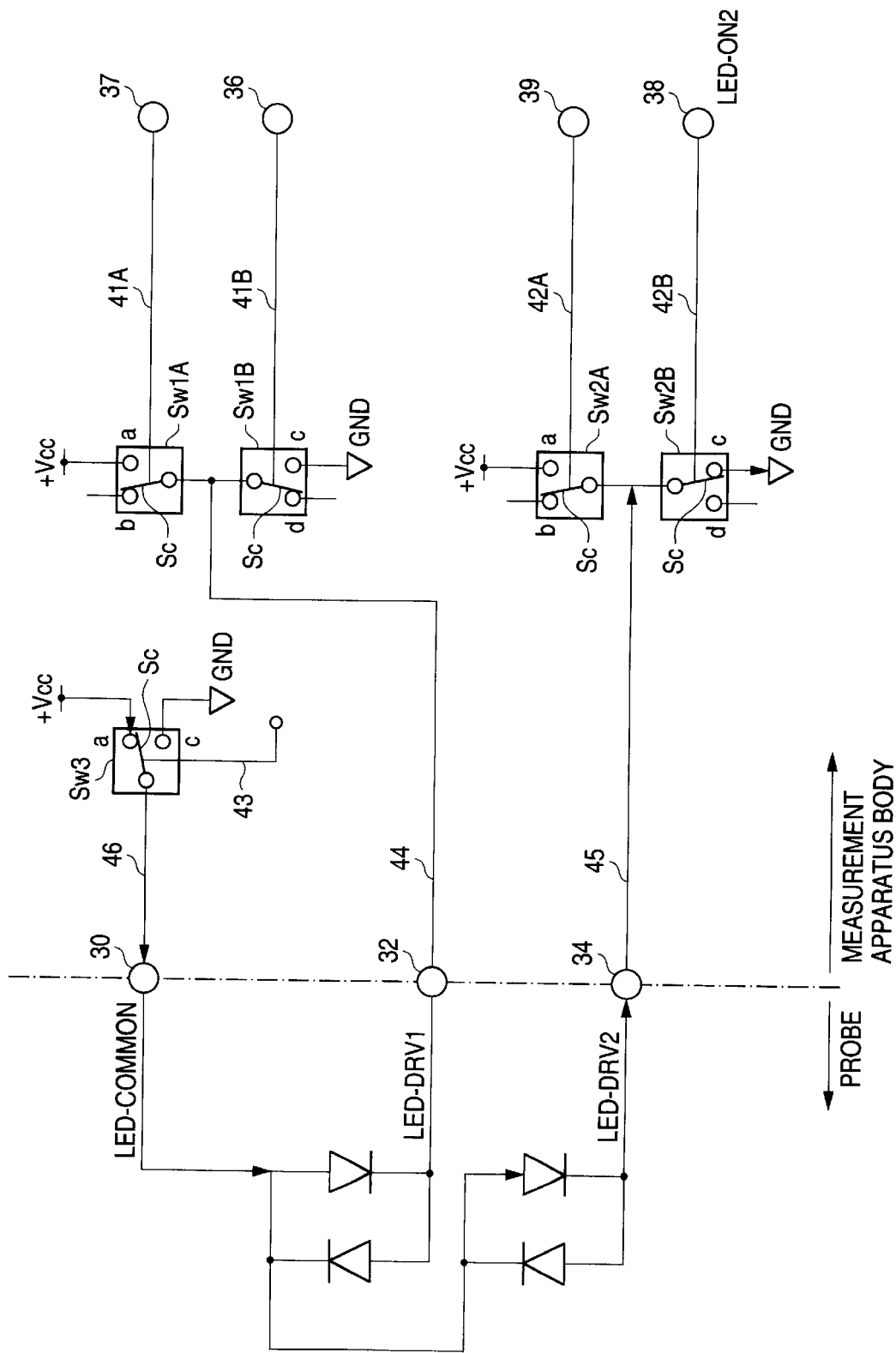
FIG. 8 is a schematic illustration showing a state in which the second light emitting diode out of the four light emitting diodes connected by the three line type connection system shown in FIG. 7 is driven.

Next, in FIG. 8, when the switching operation signal LED-ON2 is supplied to the second switching operation signal input terminal 38, the switching contact piece Sc of the driving switch Sw2B for constant current on the ground side is connected with the contact point "c", and the switching contact piece Sc of the third driving switch Sw3 for constant current is connected with the contact point "a" by the switching operation signal LED-ON2 supplied via the switching operation signal line 43. In this case, the switching contact pieces Sc of the driving switches Sw1A, Sw1B and Sw2A for constant current are respectively connected with the open contact points "b", "d" and "b". Due to the foregoing, a driving current supplied from the electric power source +Vcc on the measurement apparatus body side to the light emitting diode flows in the current supply line 46 via the connection terminal 30 of the common line LED-COMMON and the second light emitting diode LED 2 and further flows into the driving switch Sw2B for constant current on the ground side via the connection terminal 34 of the second driving line LED-DRV2 and the current supply line 45. Therefore, the second light emitting diode LED 2 can be driven.

Figure 9:
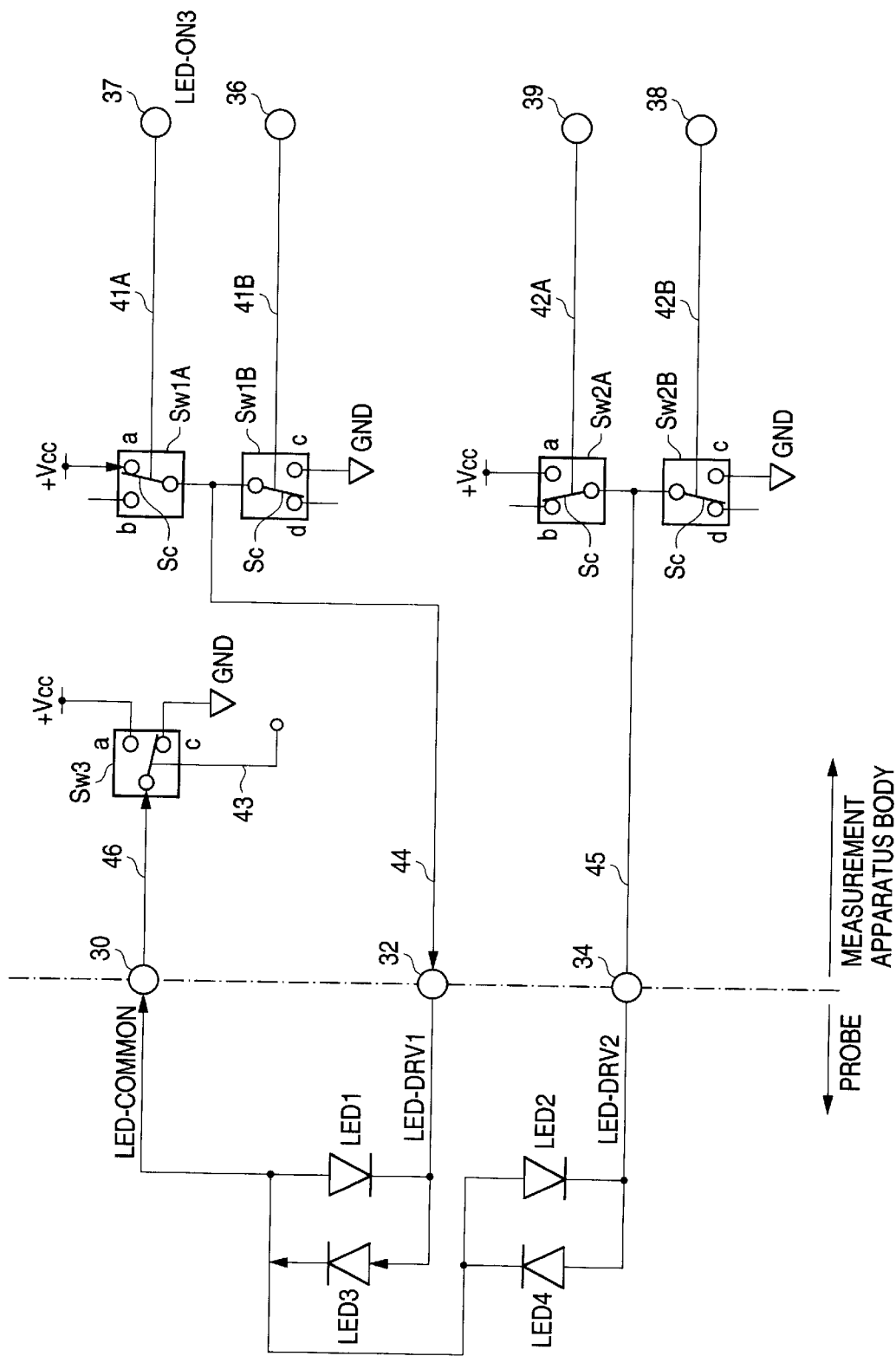
FIG. 9 is a schematic illustration showing a state in which the third light emitting diode out of the four light emitting diodes connected by the three line type connection system shown in FIG. 7 is driven.

Next, in FIG. 9, when the switching operation signal LED-ON3 is supplied to the third switching operation signal input terminal 37, the switching contact piece Sc of the driving switch Sw1A for constant current on the electric power side is connected with the contact point "a", and the switching contact piece Sc of the third driving switch Sw3 for constant current is connected with the contact point "c" by the switching operation signal LED-ON3 supplied via the switching operation signal line 43. In this case, the switching contact pieces Sc of the driving switches Sw1B, Sw2A and Sw2B for constant current are connected with the respective open contact points "d", "b" and "d". Due to the foregoing, a driving current supplied from the electric power source +Vcc on the measurement apparatus body side to the light emitting diode flows from the driving switch Sw1A for constant current on the electric power source side to GND on the ground side of the third driving switch Sw3 for constant current via the current supply line 44, the connection terminal 32 of the first driving line LED-DRV1, the third light emitting diode LED 3, the connection terminal 30 of the common line LED-COMMON and the current supply line 46. In this way, the third light emitting diode LED 3 can be driven.

Figure 10:
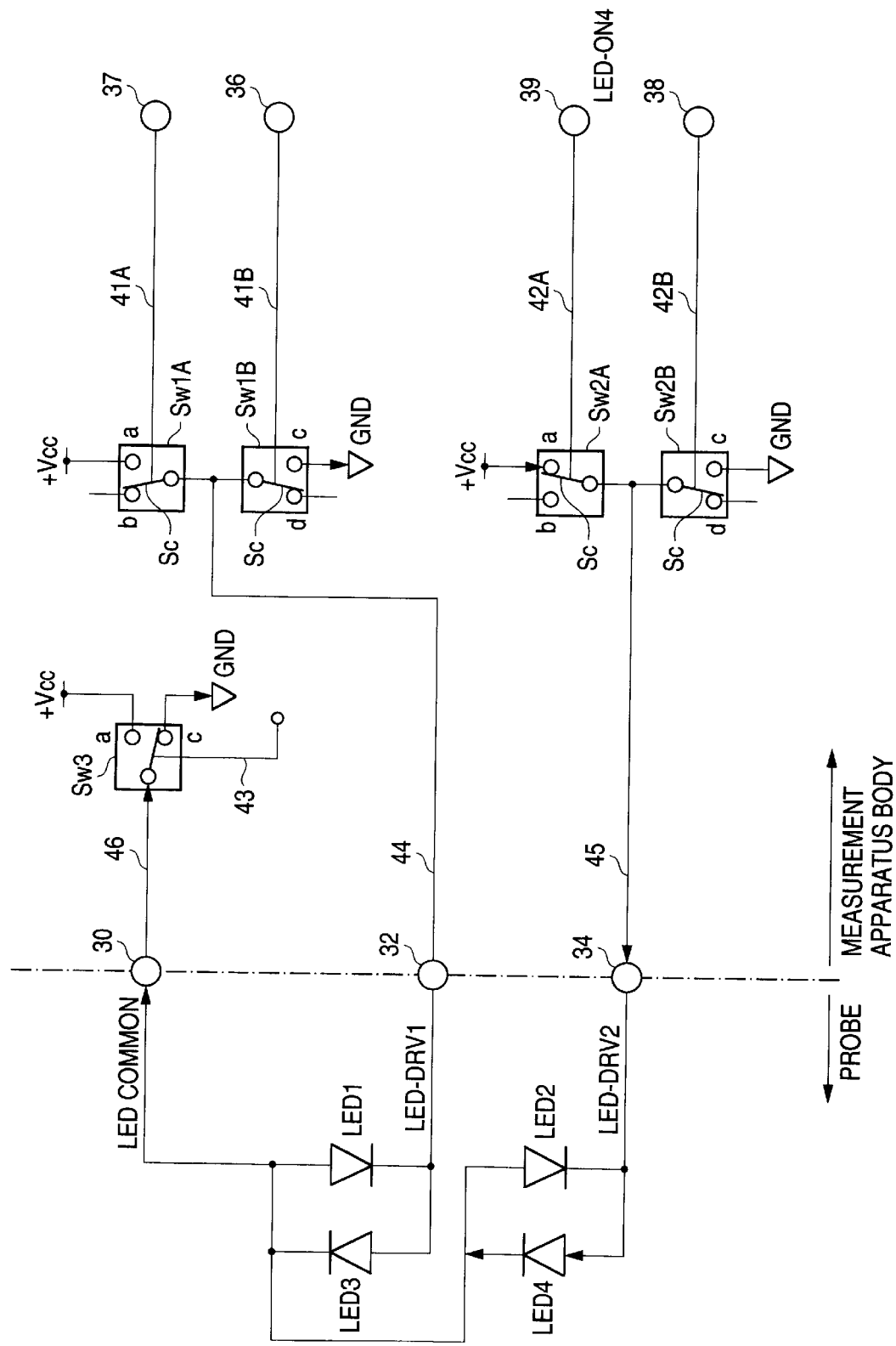
FIG. 10 is a schematic illustration showing a state in which the fourth light emitting diode out of the four light emitting diodes connected by the three line type connection system shown in FIG. 7 is driven.

Next, in FIG. 10, when the switching operation signal LED-ON4 is supplied to the fourth switching operation signal input terminal 39, the switching contact piece Sc of the driving switch Sw2A for constant current on the electric power side is connected with the contact point "a", and the switching contact piece Sc of the third driving switch Sw3 for constant current is connected with the contact point "c" by the switching operation signal LED-ON4 supplied via the switching operation signal line 43. In this case, the switching contact pieces Sc of the driving switches Sw1A, Sw1B and Sw2B for constant current are connected with the respective open contact points "b", "d" and "d". Due to the foregoing, a driving current supplied from the electric power source +Vcc on the measurement apparatus body side to the light emitting diode flows from the driving switch Sw2A for constant current on the electric power source side to GND on the ground side of the third driving switch Sw3 for constant current via the current supply line 45, the connection terminal 34 of the second driving line LED-DRV2, the fourth light emitting diode LED 4, the connection terminal 30 of the common line LED-COMMON and the current supply line 46. In this way, the third fourth emitting diode LED 4 can be driven.

When the above operation is repeated with a predetermined timed relation, the four light emitting diodes, which are connected by the three line connection method, can be successively and continuously driven.

In Second embodiment described above, the third driving switch Sw3 for constant current is provided in the current supply line 46 which directly connects the connection terminal 30 of the common line LED-COMMON with +Vcc on the electric power source side. In this third driving switch Sw3 for constant current, with respect to the switching contact piece Sc, the contact point "a" is connected with +Vcc on the electric power source side, and the contact point "c" is connected with GND on the ground side. Further, in this third driving switch Sw3 for constant current, with respect to the switching contact piece Sc, the switching operation signal line 43 for switching between the contact points "a" and "c" is arranged. The switching operation signal line 43 switches the contact point of the third driving switch Sw3 for constant current in response to the switching operation signal supplied to the switching operation signal supply lines 41A, 41B and the switching operation signal supply lines 42A, 42B of a pair of driving switches Sw1A, Sw1B for constant current and a pair of driving switches Sw2A, Sw2B for constant current.

Figure 11:
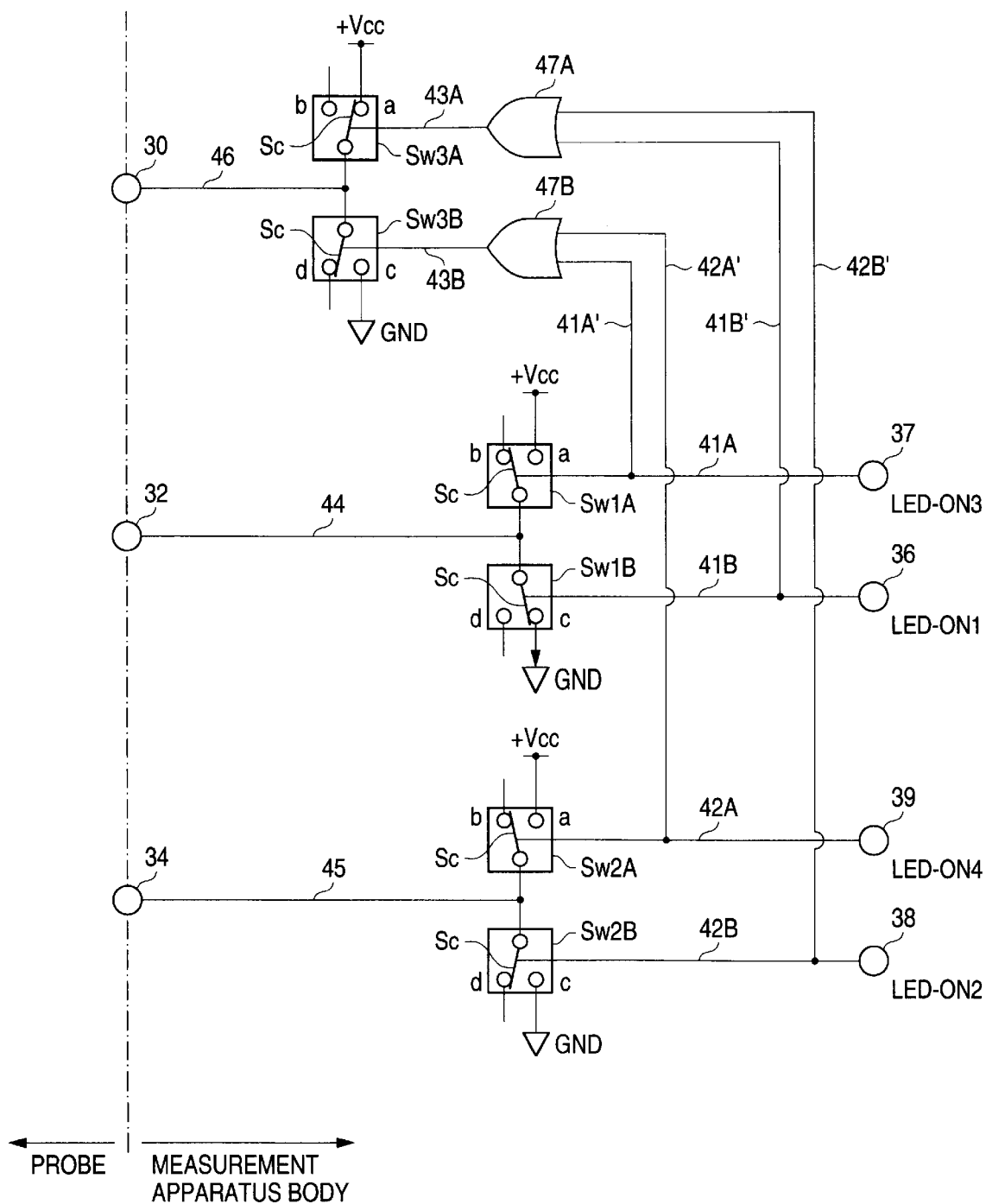
FIG. 11 is a schematic illustration showing an outline of the connection and arrangement of the circuit structure of the third driving switch for constant current in the current driving system for successively and continuously driving four light emitting diodes connected by the three line type connection system shown in FIGS. 6 and 10.

FIG. 11 is a circuit diagram showing a specific example of the circuit composed of the third driving switch Sw3 for constant current and the switching operation signal line 43 and also showing a specific example of the circuit composed of the switching operation signal supply lines 41A, 41B and the switching operation signal supply lines 42A, 42B of a pair of driving switches Sw1A, Sw1B for constant current and a pair of driving switches Sw2A, Sw2B for constant current.

In FIG. 11, the third driving switch Sw3 for constant current is composed of the driving switch Sw3A for constant current on the electric power source side and the driving switch Sw3B for constant current on the ground side. The switching operation signal supply lines 43A, 43B are respectively connected with the switching contact pieces Sc of the driving switches Sw3A, Sw3B for constant current. On the other hand, the branch lines 41A', 42A' and the branch lines 41B', 42B' respectively branch from the switching operation signal supply lines 41A, 41B and the switching operation signal supply lines 42A, 42B of a pair of driving switches Sw1A, Sw1B for constant current and a pair of driving switches Sw2A, Sw2B for constant current. The branch lines 41B', 42B' and the branch lines 41A', 42A' are respectively connected with the switching operation signal supply lines 43A, 43B via the logic OR circuits 47A, 47B. Other points of the circuit structure are the same as those of the circuit structure shown in FIG. 6. Therefore, like reference characters are used to indicate like parts in the views, and the detailed explanations will be omitted here. When the third driving switch Sw3 for constant current is arranged as described above, the light emitting diodes shown in FIGS. 7 to 10 can be successively, continuously and smoothly driven by a current.

Third Embodiment

Figure 12:
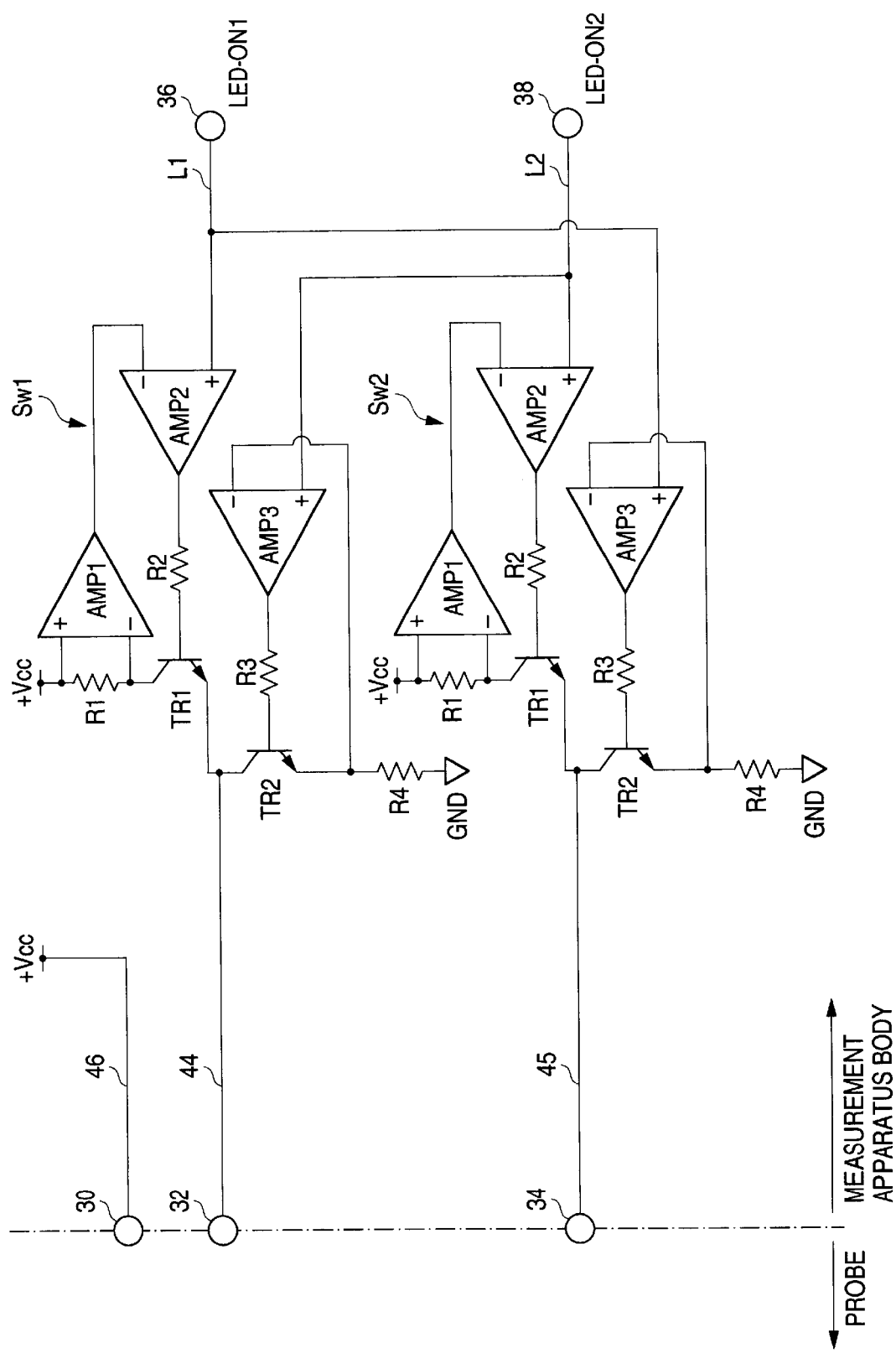
FIG. 12 is a circuit diagram showing an example of the circuit structure for respectively driving two light emitting diodes connected by the three line type or two line type connection system in the current driving system shown in FIG. 1.

Driving Circuit of Two Light Emitting Diodes Connected by Three or Two Line Connection Method FIG. 12 is a circuit diagram showing a specific example of an additional circuit provided in a light emitting diode driving circuit of a measurement apparatus body for driving two light emitting diodes connected by the three or two line connection method in First embodiment shown in FIGS. 1 to 5. In FIG. 12, as the driving switches for constant current which are respectively connected with +Vcc on the electric power source side and GND on the ground side, there are provided three differential amplifiers AMP1, AMP2, AMP3, two switching transistors TR1, TR2 and resistors R1, R2, R3, R4, which are incorporated into the circuit as shown in the drawing. Accordingly, with respect to the current supply lines 44, 45, the driving switches Sw1, Sw2, the circuit structure of which is composed as described above, are arranged.

Signal line L1 connected with the positive side input terminal of the differential amplifier AMP2 of the one driving switch Sw1 for constant current and also connected with the positive side input terminal of the differential amplifier AMP3 of the other driving switch Sw2 for constant current is connected with the first switching operation signal input terminal 36. Signal line L2 connected with the positive side input terminal of the differential amplifier AMP2 of the other driving switch Sw2 for constant current and also connected with the positive side input terminal of the differential amplifier AMP3 of the one driving switch Sw1 for constant current is connected with the second switching operation signal input terminal 38.

In the current driving system of a light emitting diode of this embodiment composed as described above, when the switching operation signals LED-ON1 and LED-ON2 are alternately supplied to the first switching operation signal input terminal 36 and the second switching operation signal input terminal 38, the light emitting diodes can be driven alternately in the same manner as that of First embodiment.

Fourth Embodiment

Figure 13:
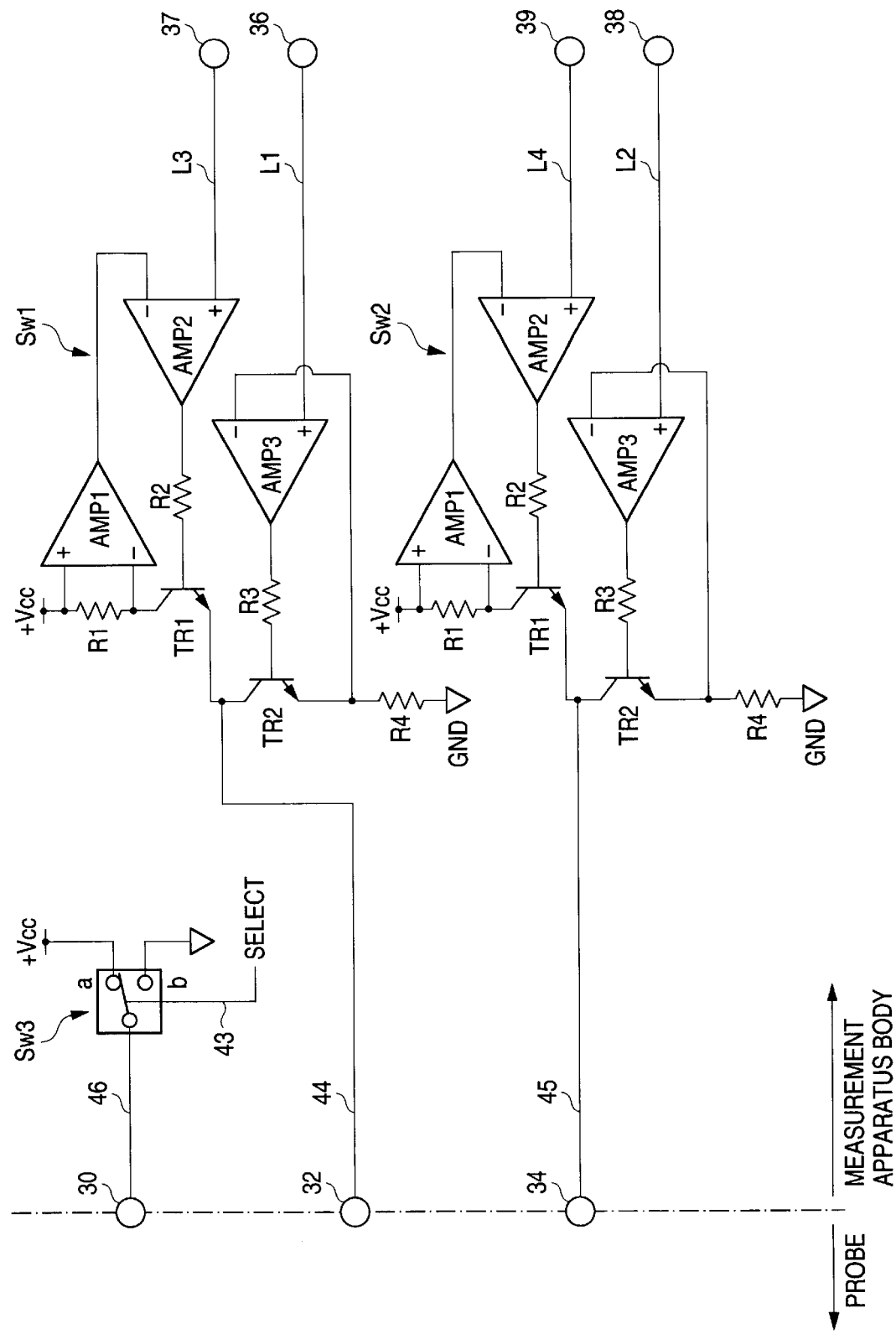
FIG. 13 is a circuit diagram showing an example of the circuit structure for respectively driving four light emitting diodes connected by the three line type connection system in the current driving system shown in FIG. 6.

Driving Circuit of Four Light Emitting Diodes Connected by Three Line Connection Method FIG. 13 is a circuit diagram showing a specific example of an additional circuit provided in a light emitting diode driving circuit of a measurement apparatus body for driving four light emitting diodes connected by the three line connection method in Second embodiment shown in FIGS. 6 to 10. In FIG. 13, as the driving switches for constant current which are respectively connected with +Vcc on the electric power source side and GND on the ground side, there are provided driving switches Sw1 and Sw2 for constant current, the circuit structure of which is the same as that of third embodiment described before.

In this embodiment, signal line L1 connected with the positive side input terminal of the differential amplifier AMP3 of the one driving switch Sw1 for constant current is connected with the first switching operation signal input terminal 36. Signal line L2 connected with the positive side input terminal of the differential amplifier AMP3 of the other driving switch Sw2 for constant current is connected with the second switching operation signal input terminal 38. Signal line L3 connected with the positive side input terminal of the differential amplifier AMP2 of the one driving switch Sw1 for constant current is connected with the third switching operation signal input terminal 37. Signal line L4 connected with the positive side input terminal of the differential amplifier AMP2 of the other driving switch Sw2 for constant current is connected with the fourth switching operation signal input terminal 39.

In the current driving system of a light emitting diode of this embodiment composed as described above, when the switching operation signal LED-ON1 to LED-ON2 is successively and continuously supplied to the first switching operation signal input terminal 36 to the fourth switching operation signal input terminal 39, the light emitting diodes can be successively and continuously driven in the same manner as that of Second embodiment. In this connection, even in this Fourth embodiment, the circuit structure and the connection arrangement shown in FIG. 11 explained in Second embodiment can be used as the third driving switch Sw3 for constant current.

Fifth Embodiment

Figure 14:
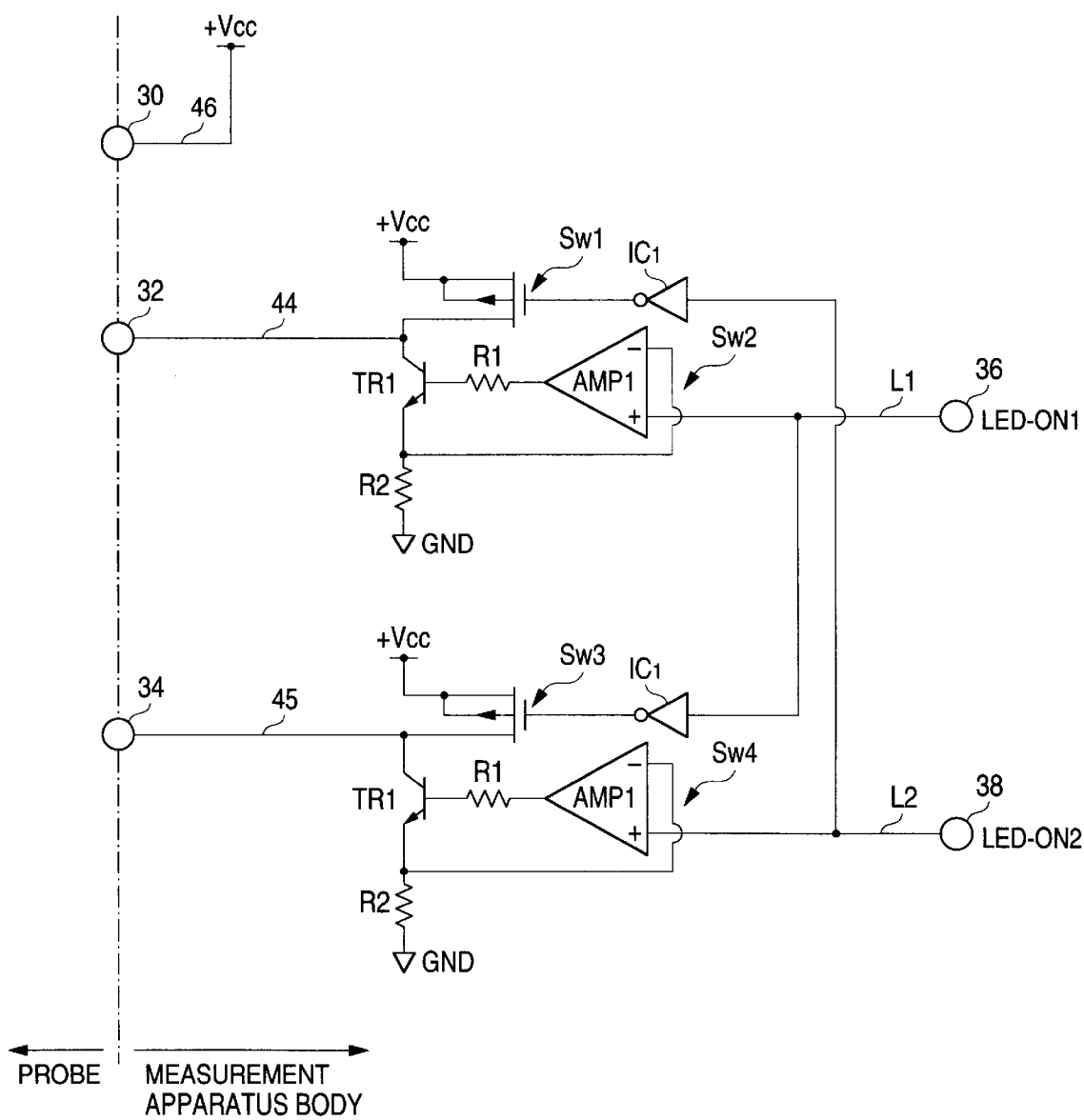
FIG. 14 is a circuit diagram showing an example of the circuit structure for respectively driving two light emitting diodes connected by the three line type or two line type connection system in the current driving system shown in FIG. 12.

Driving Circuit of Two Light Emitting Diodes Connected by Three or Two Line Type Connection Method FIG. 14 is a circuit diagram showing a specific example of an additional circuit provided in a light emitting diode driving circuit of a measurement apparatus body for driving two light emitting diodes connected by the three or two line type connection method in third embodiment shown in FIG. 12, wherein the additional circuit is made to be a driving circuit, which is less affected by noise, when an FET switch as an ON-OFF switch and a switch for constant current are actuated. In FIG. 14, the driving switches respectively connected with +Vcc on the electric power source side and GND on the ground side are composed of FET switches SW1, Sw3, an inverse circuit IC1, and the driving switches SW2, SW4 for constant current including a differential amplifier APM1, switching transistor TR1 and resistor R1. Accordingly, the current supply lines 44, 45 are respectively connected with FET switches SW1, SW3 and the driving switches SW2, SW4 for constant current, which are incorporated into the circuit structure.

The signal line L1 from the first switching operation signal input terminal 36 is connected with the positive side input terminal of the differential amplifier 1 of one driving switch SW2 for constant current and also connected with the gate terminal of the other switch SW3 via the inverse circuit IC1. The signal line L2 from the first switching operation signal input terminal 38 is connected with the positive side input terminal of the differential amplifier 1 of the other driving switch SW4 for constant current and also connected with the gate terminal of one FET switch SW1 via the inverse circuit IC1.

In the current driving system of a light emitting diode of this embodiment composed as described above, the number of the switches for constant current respectively connected with the current supply lines 44, 45 can be reduced to one as shown in FIG. 14 compared with the structure shown in FIG. 2 such that the switches are employed as two. Therefore, the driving can be stably conducted without being affected by noise. When the switching operation signals LED-ON1 and LED-ON2 are alternately given to the first switching operation signal input terminal 36 and the second switching operation signal input terminal 38, the light emitting diodes can be alternately driven.

Sixth Embodiment

Figure 15:
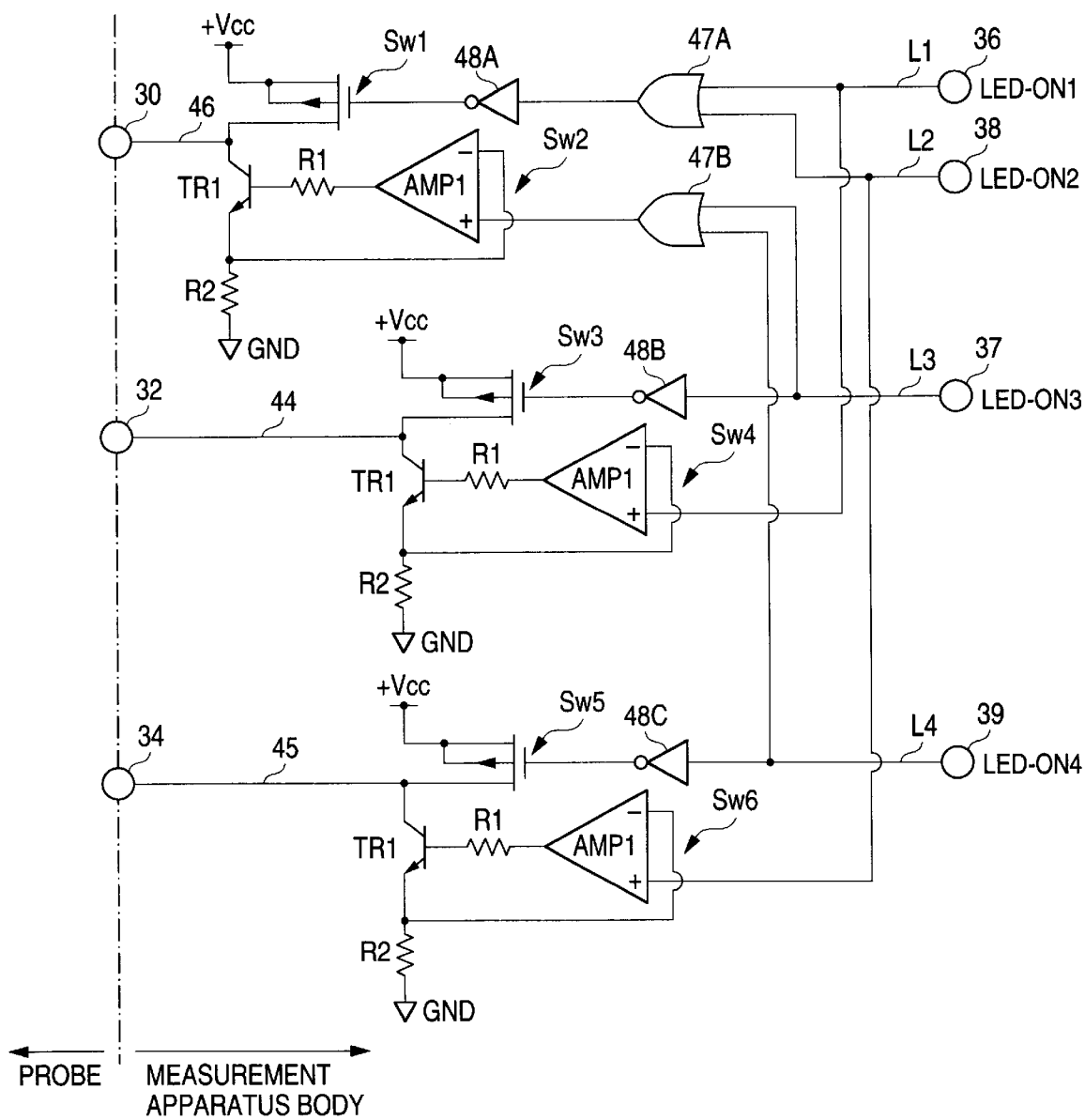
FIG. 15 is a circuit diagram showing an example of the circuit structure for respectively driving two light emitting diodes connected by the three line type or two line type connection system in the current driving system shown in FIG. 13.
Figure 16:
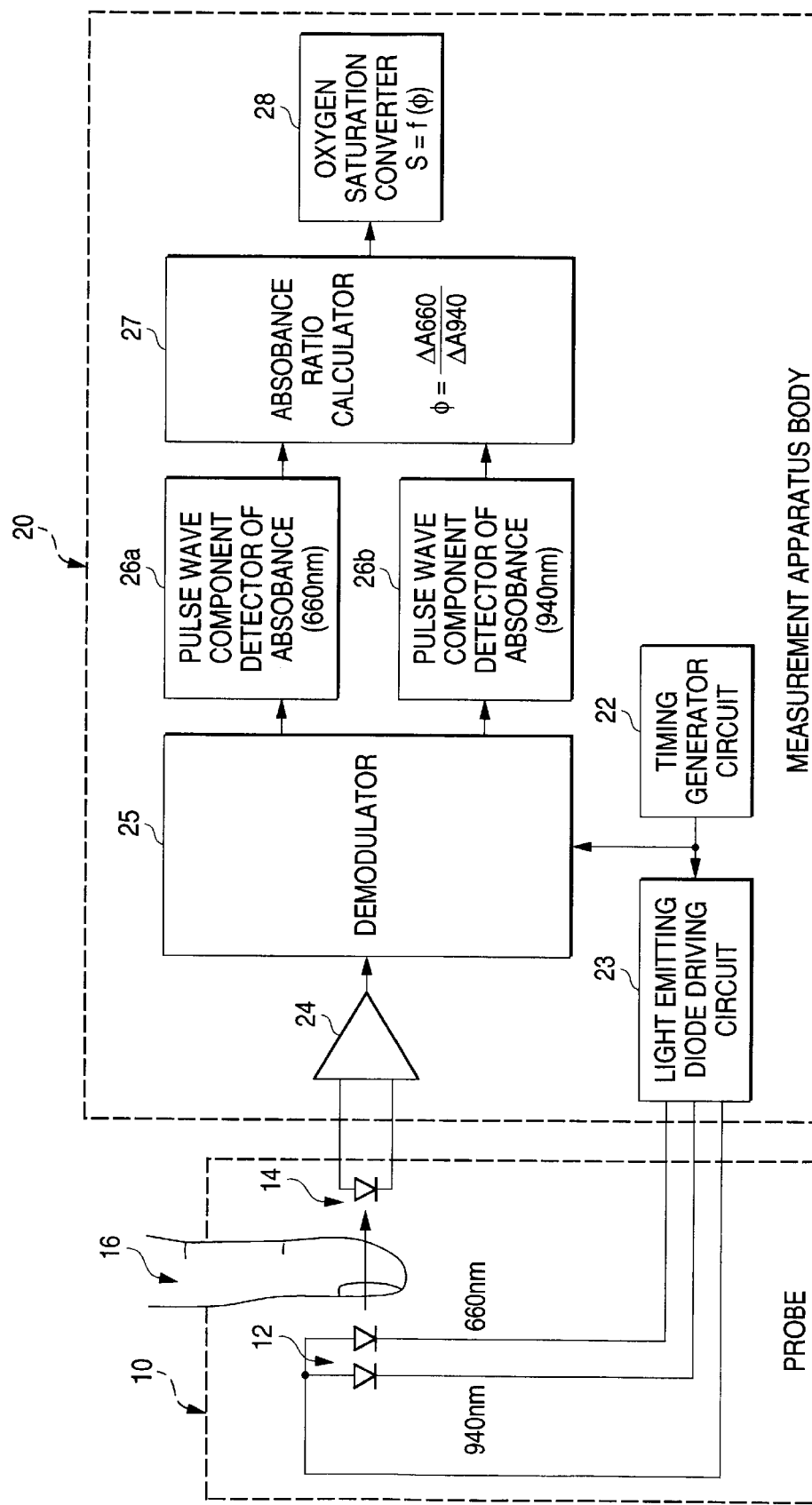
FIG. 16 is a block circuit diagram showing the basic circuit structure of a pulse oximeter.
Figure 17:
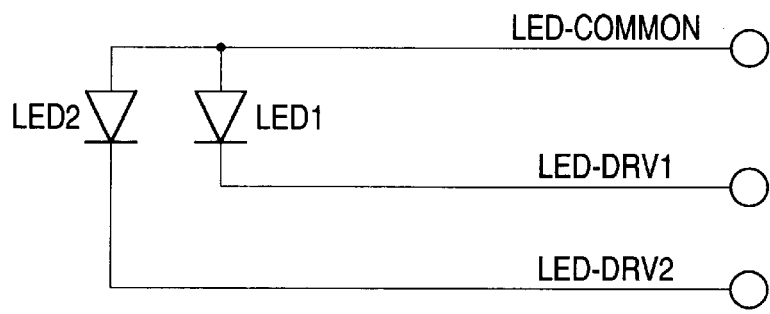
FIG. 17 is a schematic illustration showing a system in which two light emitting diodes in a probe of a conventional oximeter are connected by the three line type connection method.
Figure 18:
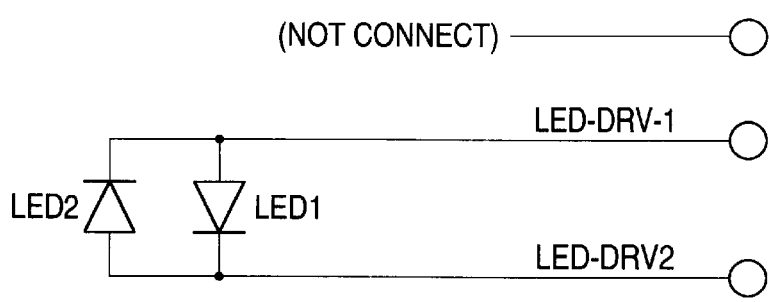
FIG. 18 is a schematic illustration showing a system in which two light emitting diodes in a probe of a conventional oximeter are connected by the two line type connection method.
Figure 19:
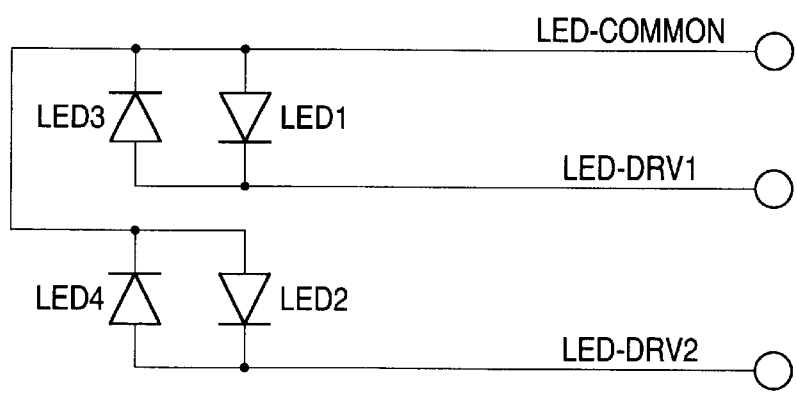
FIG. 19 is a schematic illustration showing a system in which four light emitting diodes in a probe of a conventional oximeter are connected by the three line type connection method.
Figure 20:
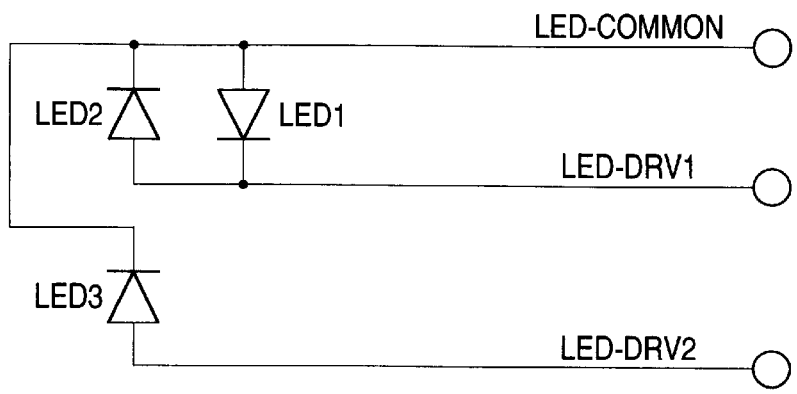
FIG. 20 is a schematic illustration showing a system in which three light emitting diodes in a probe of a conventional oximeter are connected by the three line type connection method.

Driving Circuit of Four Light Emitting Diodes Connected by Three Line Type Connection Method FIG. 15 is a circuit diagram showing a specific example of an additional circuit provided in a light emitting diode driving circuit of a measurement apparatus body for driving four light emitting diodes connected by the three line type connection method in Fourth embodiment shown in FIG. 13, wherein the additional circuit is made to be a driving circuit, which is less affected by noise, when an FET switch as an ON-OFF switch and a switch for constant current are actuated. In FIG. 15, the driving switches respectively connected with +Vcc on the electric power source side and GND on the ground side are composed of FET switches SW1, Sw3, SW5, an inverse circuit IC1, and the driving switches SW2, SW4, SW6 for constant current including a differential amplifier APM1, switching transistor TR1 and resistor R1. Accordingly, the current supply lines 46, 44, 45, are respectively connected with FET switches SW1, SW3, SW5 and the driving switches SW2, SW4, SW6 for constant current, which are incorporated into the circuit structure.

In this embodiment, the gate terminal of the switch SW1 is connected with the reverse circuit 48 and further connected with the logic OR circuit 47A with which the signal line L1 connected with the first switching operation signal input terminal 36 is connected and also the signal line L2 connected with the second switching operation signal input terminal 38 is connected. The positive side input terminal of the differential amplifier AMP1 composing the switch SW2 for constant current is connected with the signal line L3, which is connected with the third switching operation signal input terminal 37, and also connected with the signal line L4, which is connected with the fourth switching operation signal input terminal 39, via the logic OR circuit 47B. The signal line L3 which is connected with the third switching operation signal input terminal 37 is connected to the gate terminal of FET switch SW3 via the inverse circuit 48B. constantThe signal line L1 which is connected with the first switching operation signal input terminal 36 is connected to the positive side input terminal of the differential amplifier AMP 1 composing the switch SW4 for constant current. The signal line L4 which is connected with the fourth switching operation signal input terminal 39 is connected to the gate terminal of FET switch SW5 via the inverse circuit 48C. constantThe signal line L2 which is connected with the second switching operation signal input terminal 38 is connected to the positive side input terminal of the switch Sw6 for constant current.

In the current driving system of a light emitting diode of this embodiment composed as described above, the number of the switches for constant current respectively connected with the current supply lines 44, 45, 46 can be reduced to one as shown in FIG. 15 compared with the structure shown in FIG. 13 such that the switches are employed as two. Therefore, the driving can be stably conducted without being affected by noise. When the switching operation signals LED-ON1, LED-ON2, LED-ON3 and LED-ON4 are alternately given to the first switching operation signal input terminal 36, the second switching operation signal input terminal 38, the third switching operation signal input terminal 37 and the fourth switching operation signal input terminal 39, the light emitting diodes can be alternately driven.

Preferred embodiments of the present invention are explained above. However, it should be noted that the present invention is not limited to the above specific embodiments, and variations may be made by one skilled in the art without departing the spirit and scope of the present invention. For example, in the system in which three light emitting diodes are connected by the three line method, it can be easily executed by conducting the driving control in which one light emitting diode is omitted in Second embodiment. For example, the driving switch for switching the current supply line to the electric power source side or the ground side is not limited to a driving switch for constant current, but it is possible to use a driving switch for voltage instead.

As can be seen in the above embodiments, the present invention provides a current driving system of a light emitting diode including an apparatus for measuring the concentration of light absorbing material in a living tissue, the apparatus for measuring the concentration of light absorbing material having a probe attached to the living tissue and also having a measurement apparatus body combined with the probe for calculating the concentration of light absorbing material in the living tissue, the probe having a light emitting section composed of at least two light emitting diodes of different wave lengths of emitted light and also having a light receiving section composed of a photo-diode for receiving light emitted from the light emitting section and transmitted through the living tissue, the light emitting diodes being successively and continuously driven by a light emitting diode driving circuit arranged in the measurement apparatus body, the current driving system of a light emitting diode provided in that: three current supply lines and connection terminals thereof for respectively driving the light emitting diodes on the probe side are arranged in a light emitting diode driving circuit on the measurement apparatus body side; a pair of driving switches for constant current having contact points to be switched to the electric power source side or the ground side are respectively connected with the two current supply lines among the three current supply lines; and a switching operation signal supply line is arranged for successively and continuously driving the light emitting diodes by supplying a switching operation signal for switching the contact points on the electric power source side or on the ground side to the pair of driving switches for constant current. Due to the above arrangement, it is possible to provide a current driving system of a light emitting diode provided in that: only when a simple additional circuit is arranged in a light emitting diode driving circuit, various probes can be used being made compatible with each other when they are connected with the measurement apparatus body without changing the basic structure of the circuit of the measurement apparatus body and without providing a redundant connection means and without being restricted by the lead connection system of the light emitting diode on the probe side.

What is claimed is:

1. A current driving system of a light emitting diode comprising:
   an apparatus for measuring a concentration of light absorbing material in a living tissue, the apparatus including:
      a probe adapted to be attached to a living tissue, the probe having a light emitting section having at least two light emitting diodes emitting lights of different wavelengths, the probe further having a light receiving section defined by a photo-diode for receiving light emitted from the light emitting section after being transmitted through the living tissue;

a measurement apparatus body, attached with the probe, for calculating the concentration of light absorbing material in the living tissue, said at least two light emitting diodes being successively and continuously driven by a light emitting diode driving circuit arranged in the measurement apparatus body;

three current supply lines and connection terminals thereof for respectively driving said at least two light emitting diodes;

a first pair of driving switches connected to a first of the three current supply lines, a first switch among the first pair having contact points switched to an electric power source and a second switch among the first pair switched to a ground;

a second pair of driving switches connected to a second of the three current supply lines, a first switch among the second pair having contact points switched to the electric power source and the second switch among the second pair switched to the ground; and switching operation signal supply lines arranged for successively and continuously driving the light emitting diodes by supplying switching operation signals to the first and second pair of driving switches, wherein the driving switches and the signal supply line is disposed inside the measurement apparatus body.

2. A current driving system of a light emitting diode according to claim 1, wherein the three current supply lines are respectively connected with a first driving line and a second driving line of the probe and also connected with a common line so that the at least two light emitting diodes can be successively and continuously driven.

3. A current driving system of a light emitting diode according to claim 1, wherein the switching operation signal supply lines are connected and arranged so that the light emitting diodes can be successively and continuously driven when a contact point switching operation is simultaneously conducted on the first and second switches of the first pair of driving switches and the first and second switches of the second pair of driving switches.

4. A current driving system of a light emitting diode according to claim 1, wherein the three current supply lines for respectively driving the light emitting diodes are set in such a manner that the first and second current supply lines, with which the pair of driving switches are connected, are connected with a first driving line and a second driving line for respectively and successively driving at least two light emitting diodes on the probe, and the third current supply line is set as a dummy terminal.

5. A current driving system of a light emitting diode according to claim 1, wherein the switching operation signal supply lines are connected and arranged so that the contact points switched and connected with the electric power and the ground of the respective driving switches are independently switched by the first and second pair of driving switches respectively connected with the first and second current supply lines, a third driving switch having a contact point for switching between the electric power source and the ground is arranged in the third current supply line, and a third switching operation signal supply line is connected and arranged which is used for switching the contact point of the third driving switch corresponding to the switching operation signal supplied to the switching operation signal supply line of the first and second pair of driving switches.

6. A current driving system of a light emitting diode according to claim 5, wherein four switching operation signal supply lines are respectively connected and arranged as a switching operation signal supply line for switching the contact points of the two pairs of driving switches and as a switching operation signal supply line for switching the contact points of the third driving switch.

7. A current driving system of a light emitting diode according to claim 1, wherein the three current supply lines for respectively driving the light emitting diodes are arranged in such a manner that three or four light emitting diodes, in which a first two light emitting diodes are connected in reverse-parallel to each other on the probe and a second two light emitting diodes are connected in reverse-parallel to each other, and the first two and the second two light emitting diodes are respectively connected with the first driving line and the second driving line, and further the diodes are successively and continuously driven, and further the diodes are connected with the common line.

8. A current driving system of a light emitting diode according to claim 7, wherein the probe is arranged in such a manner that the first two reverse-parallel diodes are connected between the common line and the first driving line, and the second two reverse-parallel diodes are connected with the common line and the second driving line, so that the four light emitting diodes are respectively, successively and continuously driven.

9. A current driving system of a light emitting diode according to claim 7, wherein the switching operation signal supply line is connected and arranged so that the contact points switched and connected with the electric power source and the ground of the respective driving switches are independently switched by the pair of driving switches respectively connected with the two current supply lines, a third driving switch having a contact point for switching between the electric power source and the ground is arranged in the other current supply line, and a switching operation signal supply line is connected and arranged which is used for switching the contact point of the third driving switch corresponding to the switching operation signal supplied to the switching operation signal supply line of the two pairs of driving switches.

10. A current driving system of a light emitting diode according to claim 1, wherein the three current supply lines for respectively driving the light emitting diodes are arranged in such a manner that three or four light emitting diodes, in which a first two light emitting diodes are connected in reverse-parallel to each other on the probe , and the first two and a third light emitting diodes are respectively connected with the first driving line and the second driving line, and further the diodes are successively and continuously driven, and further the diodes are connected with the common line.

11. A current driving system of a light emitting diode according to claim 10, wherein the probe is arranged in such a manner that the first two reverse-parallel diodes are connected between the common line and the first driving line, and the third light emitting diode is connected with the common line and the second driving line, so that the three light emitting diodes are respectively, successively and continuously driven.

12. A current driving system of a light emitting diode according to claim 1, wherein at least one driving switch includes an ON-OFF switch and a switch for constant current.

13. A current driving system of a light emitting diode comprising:

an apparatus for measuring a concentration of light absorbing material in a living tissue, the apparatus including:

a measurement apparatus body, capable of attaching with a probe, for calculating the concentration of light absorbing material in the living tissue, a light emitting diode driving circuit arranged in the measurement apparatus body, the light emitting diode circuit being capable of continuously and successively driving at least two light emitting diodes in the probe;

three current supply lines and connection terminals thereof for respectively driving said at least two light emitting diodes;

a first pair of driving switches connected to a first of the three current supply lines, a first switch among the first pair having contact points switched to an electric power source and a second switch among the first pair switched to a ground;

a second pair of driving switches connected to a second of the three current supply lines, a first switch among the second pair having contact points switched to the electric power source and the second switch among the second pair switched to the ground; and switching operation signal supply lines arranged for successively and continuously driving the light emitting diodes by supplying switching operation signals to the first and second pair of driving switches, wherein the driving switches and the signal supply line are disposed inside the measurement apparatus body.

14. A current driving system of a light emitting diode according to claim 13, wherein the three current supply lines are respectively capable of being connected with a first driving line and a second driving line of the probe and also connected with a common line so that the at least two light emitting diodes can be successively and continuously driven.

15. A current driving system of a light emitting diode according to claim 13, wherein the switching operation signal supply lines are connected and arranged so that the light emitting diodes can be successively and continuously driven when a contact point switching operation is simultaneously conducted on the first and second switches of the first pair of driving switches and the first and second switches of the second pair of driving switches.

16. A current driving system of a light emitting diode according to claim 13, wherein the three current supply lines for respectively driving the light emitting diodes are set in such a manner that the first and second current supply lines, with which the pair of driving switches are connected, are connected with a first driving line and a second driving line for respectively and successively driving at least two light emitting diodes on the probe, and the third current,supply line is set as a dummy terminal.

17. A current driving system of a light emitting diode according to claim 13, wherein the switching operation signal supply lines are connected and arranged so that the contact points switched and connected with the electric power and the ground of the respective driving switches are independently switched by the first and second pair of driving switches respectively connected with the first and second current supply lines, a third driving switch having a contact point for switching between the electric power source and the ground is arranged in the third current supply line, and a third switching operation signal supply line is connected and arranged which is used for switching the contact point of the third driving switch corresponding to the switching operation signal supplied to the switching operation signal supply line of the first and second pair of driving switches.

18. A current driving system of a light emitting diode according to claim 17, wherein four switching operation signal supply lines are respectively connected and arranged as a switching operation signal supply line for switching the contact points of the two pairs of driving switches and as a switching operation signal supply line for switching the contact points of the third driving switch.

19. A current driving system of a light emitting diode according to claim 13, wherein the three current supply lines for respectively driving the light emitting diodes are arranged in such a manner that three or four light emitting diodes, in which a first two light emitting diodes are connected in reverse-parallel to each other on the probe and a second two light emitting diodes are connected in reverse-parallel to each other, and the first two and the second two light emitting diodes are respectively connected with the first driving line and the second driving line, and further the diodes are successively and continuously driven, and further the diodes are connected with a common line.

20. A current driving system of a light emitting diode according to claim 19, wherein the probe is arranged in such a manner that the first two reverse-parallel diodes are connected between the common line and the first driving line, and the second two reverse-parallel diodes are connected with the common line and the second driving line, so that the four light emitting diodes are respectively, successively and continuously driven.

21. A current driving system of a light emitting diode according to claim 19, wherein the switching operation signal supply line is connected and arranged so that the contact points switched and connected with the electric power source and the ground of the respective driving switches are independently switched by the pair of driving switches respectively connected with the two current supply lines, a third driving switch having a contact point for switching between the electric power source and the ground is arranged in the other current supply line, and a switching operation signal supply line is connected and arranged which is used for switching the contact point of the third driving switch corresponding to the switching operation signal supplied to the switching operation signal supply line of the two pairs of driving switches.

22. A current driving system of a light emitting diode according to claim 13, wherein the three current supply lines for respectively driving the light emitting diodes are arranged in such a manner that three or four light emitting diodes, in which a first two light emitting diodes are connected in reverse-parallel to each other on the probe, and the first two and a third light emitting diodes are respectively connected with the first driving line and the second driving line, and further the diodes are successively and continuously driven, and further the diodes are connected with a common line.

23. A current driving system of a light emitting diode according to claim 22, wherein the system is capable of being arranged with the probe in such a manner that the first two reverse-parallel diodes are connected between the common line and the first driving line, and the third light emitting diode is connected with the common line and the second driving line, so that the three light emitting diodes are respectively, successively and continuously driven.

24. A current driving system of a light emitting diode according to claim 13, wherein at least one driving switch includes an ON-OFF switch and a switch for constant current.

* * * * *